US 9,096,886 B2

(12) United States Patent
Fink et al.

(10) Patent No.: US 9,096,886 B2
(45) Date of Patent: Aug. 4, 2015

(54) METHOD FOR THE DETERMINATION OF BOTULINUM NEUROTOXIN BIOLOGICAL ACTIVITY

(75) Inventors: Klaus Fink, Cologne (DE); Martin Vey, Wayne, PA (US)

(73) Assignee: MERZ PHARMA GmbH & CO. KGaA, Frankfurt am Main (DE)

(*) Notice: Subject to any disclaimer, the term of this patent is extended or adjusted under 35 U.S.C. 154(b) by 0 days.

(21) Appl. No.: 14/004,259

(22) PCT Filed: Mar. 9, 2012

(86) PCT No.: PCT/EP2012/054143
§ 371 (c)(1),
(2), (4) Date: Sep. 10, 2013

(87) PCT Pub. No.: WO2012/123370
PCT Pub. Date: Sep. 20, 2012

(65) Prior Publication Data
US 2014/0004541 A1    Jan. 2, 2014

Related U.S. Application Data

(60) Provisional application No. 61/464,982, filed on Mar. 11, 2011.

(30) Foreign Application Priority Data

Mar. 11, 2011  (EP) .................................. 11157812

(51) Int. Cl.
*A61K 38/00* (2006.01)
*A61K 38/48* (2006.01)
(Continued)

(52) U.S. Cl.
CPC ............... *C12Q 1/37* (2013.01); *C12N 9/6472* (2013.01); *C12N 9/6475* (2013.01);
(Continued)

(58) Field of Classification Search
CPC .... A61K 2300/00; A61K 38/00; A61K 38/48
USPC ....................................... 530/350; 424/94.63
See application file for complete search history.

(56) References Cited

U.S. PATENT DOCUMENTS 6,221,355 B1 * 4/2001 Dowdy ...................... 424/192.1
8,575,009 B2 * 11/2013 Sleight et al. ............... 438/479
(Continued)

FOREIGN PATENT DOCUMENTS

| EP | 1 926 744 | 4/2010 |
|---|---|---|
| WO | 00/34308 | * 6/2000 |
| WO | WO 2005/076785 | 5/2005 |

OTHER PUBLICATIONS

Steiner, Harald et al, FEBS Letters, vol. 463, 1999, pp. 245-249, An in vivo assay for identification of target proteases which cleave membrane associated substrates.*
Black, Margaret E et al, PNAS, vol. 93, Apr. 1996, pp. 3525-3529, Creation of drug specific herpes simplex virus type 1 thymidine kinase mutants for gene therapy.*
Hawkins, V et al, Journal of Biomedical Science, 1999, Nov.-Dec., vol. 6(6), pp. 433-438, Kynostatin and 17beta-estradiol prevent the apoptotic death of human neuroblastoma cells exposed to HIV-1 protease (abstract only).*

(Continued)

*Primary Examiner* — Albert Navarro
*Assistant Examiner* — Ginny Portner
(74) *Attorney, Agent, or Firm* — Hueschen and Sage

(57) ABSTRACT

The present invention relates to means and methods for determining neurotoxin activity. Specifically, it relates to a polypeptide having caspase activity comprising a large subunit and a small subunit wherein the caspase further comprises a neurotoxin cleavage site which upon cleavage activates the caspase activity. Also encompassed are polynucleotides encoding the polypeptides as well as vectors or host cells comprising the polynucleotides. The present invention further relates to a method for determining neurotoxin activity in a sample based on the polypeptide of the invention as well as the use of the polypeptide for determining neurotoxin activity in a sample, in general.

12 Claims, 13 Drawing Sheets

Figure 1:
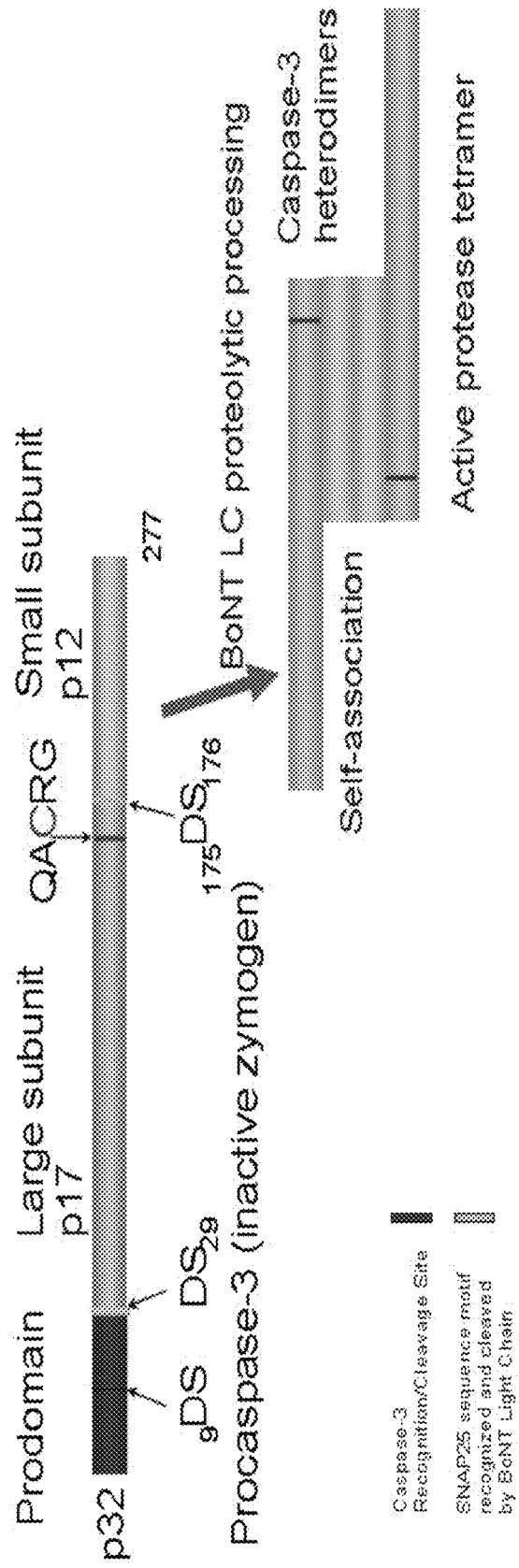

(51) Int. Cl.
   *C12Q 1/37* (2006.01)
   *G01N 33/50* (2006.01)
   *C12N 9/64* (2006.01)

(52) U.S. Cl.
   CPC .. *C12Y 304/2206* (2013.01); *C12Y 304/22055* (2013.01); *C12Y 304/22056* (2013.01); *C12Y 304/22059* (2013.01); *C12Y 304/22061* (2013.01); *C12Y 304/22062* (2013.01); *C12Y 304/22063* (2013.01); *G01N 33/5014* (2013.01); *G01N 2333/33* (2013.01); *G01N 2510/00* (2013.01)

(56) References Cited

U.S. PATENT DOCUMENTS

| | | | |
|---|---|---|---|
| 2003/0054000 A1* | 3/2003 | Dowdy | 424/94.63 |
| 2003/0100707 A1* | 5/2003 | Hwang et al. | 530/350 |
| 2004/0018529 A1* | 1/2004 | Li et al. | 435/6 |
| 2005/0153310 A1* | 7/2005 | Fan et al. | 435/6 |
| 2005/0271647 A1* | 12/2005 | Baltimore et al. | 424/94.64 |
| 2009/0170131 A1* | 7/2009 | Gelovani et al. | 435/7.23 |
| 2010/0093552 A1* | 4/2010 | Panja | 506/7 |
| 2010/0216711 A1* | 8/2010 | Grallert et al. | 514/12 |
| 2014/0030725 A1* | 1/2014 | Binkowski et al. | 435/6.13 |
| 2014/0141450 A1* | 5/2014 | Hu | 435/7.4 |

OTHER PUBLICATIONS

Altschul, et al., 1990, J Mol Biol, vol. 215, p. 403-410.
Ellis, et al., 1991, Annu Rev Cell Biol, 7: p. 663-698.
Fischer, et al., 2007, PNAS, vol. 104, No. 25, p. 10447-10452.
Higgins, et al., 1989, CABIOS, vol. 5, No. 2, p. 151-153.
Jeppsen, et al., 2008, J Biol Chem, vol. 283, No. 10, p. 6126-6135.
Jost, et al., 2007, Drugs, vol. 67, No. 5, p. 669-683.
Krieglstein, et al., 1990, Eur J Biochem, vol. 188, p. 39-45.
Krieglstein, et al., 1991, Eur J Biochem, vol. 202, p. 41-51.
Krieglstein, et al., 1994, J Protein Chem, vol. 13, No. 1, p. 49-57.
Miura, et al., 1993, Cell, vol. 75(4), p. 653-660.
Needleman, et al., 1970, J Mol Biol, vol. 48, p. 443-453.
Smith, et al., 1981, Adv Appl Math, vol. 2, p. 482-489.
Tait. 2008, J Nuclear Medicine vol. 49(10): p. 1573-1576.
Tait, 2006, J Nuclear Medicine, vol. 47, No. 9, p. 1546-1553.
Yuan, et al., 1992, Development, vol. 116(2): p. 309-320.
Yuan, et al., 1993, Cell, vol. 75(4), p. 641-652.
International Search Report for PCT/EP2012/054143 of Apr. 5, 2012.
Kegel, et al., Toxicology in Vitro, vol. 21, No. 8, p. 1641-1649, Nov. 12, 2007.
Pablo Fuentes-Prior, et al., Biochemical Journal, vol. 384, No. 2, p. 201-232, Dec. 1, 2004.
IPRP for PCT/EP2012/054143.

* cited by examiner

METHOD FOR THE DETERMINATION OF BOTULINUM NEUROTOXIN BIOLOGICAL ACTIVITY

The present invention relates to means and methods for determining neurotoxin activity. Specifically, it relates to a polypeptide having caspase activity comprising a large subunit and a small subunit wherein said caspase further comprises a neurotoxin cleavage site which upon cleavage activates the caspase activity. Also encompassed are polynucleotides encoding said polypeptides as well as vectors or host cells comprising the polynucleotides. The present invention further relates to a method for determining neurotoxin activity in a sample based on the polypeptide of the invention as well as the use of said polypeptide for determing neurotoxin activity in a sample, in general.

*Clostridium botulinum* and *Clostridium tetani* produce highly potent neurotoxins, i.e. botulinum toxins (BoNTs) and tetanus toxin (TeNT), respectively. These Clostridial neurotoxins specifically bind to neuronal cells and disrupt neurotransmitter release. Each toxin is synthesized as an inactive unprocessed approximately 150 kDa single-chain protein. The posttranslational processing involves formation of disulfide bridges, and limited proteolysis (nicking) by bacterial protease(s). Active dichain neurotoxin consists of two chains, an N-terminal light chain of approx. 50 kDa and a heavy chain of approx. 100 kDa linked by a disulfide bond. Neurotoxins structurally consist of three domains, i.e. the catalytic light chain, the heavy chain encompassing the translocation domain (N-terminal half) and the receptor binding domain (C-terminal half), see Krieglstein 1990, Eur J Biochem 188, 39; Krieglstein 1991, Eur J Biochem 202, 41; Krieglstein 1994, J Protein Chem 13, 49.

*Clostridium botulinum* secretes seven antigenically distinct serotypes designated A to G of the BoNTs. All serotypes together with the related TeNT secreted by *Clostridium tetani*, are zinc ($Zn^{2+}$)-dependent endoproteases that block synaptic exocytosis by cleaving SNARE proteins and, in particular in the case of BoNT/A, C or E, SNAP-25. BoNTs cause, inter alia, the flaccid muscular paralysis seen in botulism, see Fischer 2007, PNAS 104, 10447.

Despite its toxic effects, BoNTs have been used as a therapeutic agents in a large number of diseases. BoNT serotype A (BoNT/A) was approved for human use in the United States in 1989 for the treatment of strabism, blepharospasm, and other disorders. It is commercially available as a protein preparation, for example, under the tradename BOTOX (Allergan Inc) under the tradename DYSPORT (Ipsen Ltd). For therapeutic application the complex is injected directly into the muscle to be treated. At physiological pH, the toxin is released from the protein complex and the desired pharmacological effect takes place. An improved BoNT/A preparation being free of complexing proteins is available under the tradename XEOMIN (Merz Pharmaceuticals GmbH).

BoNTs, in principle, weaken voluntary muscle strength and are, therefore, effective therapeutic agents for the therapy of diseases such as strabism, focal dystonia, including cervical dystonia, and benign essential blepharospasm or spasticity. They have been further shown to relief hemifacial spasm, and focal spasticity, and moreover, to be effective in a wide range of other indications, such as gastrointestinal disorders, hyperhidrosis, and cosmetic wrinkle correction, see Jost 2007, Drugs 67, 669.

The determination of the biological activity is important as a safety measure, for quality control and for quantification purposes. The mouse LD50 assay is currently the only reliable assay for quantifying the biological activity of neurotoxins and for assessing their therapeutic potential and/or their toxicity. Said assay is also accepted for quality control purposes during manufacture of neurotoxin. In the mouse LD50 bioassay, lethal and sub-lethal concentrations of a sample containing the neurotoxin polypeptide have to be injected into at least 120 animals. The number of killed animals over an observation period of 72 hours allows determining the neurotoxin polypeptide concentration in the sample. Apparent drawbacks of this assay are the high number of animals which will be sacrificed and the high level of stress and pain for said animals during the test.

In vitro assays which have been proposed so far are based on determining SNAP-25 cleavage in a cell free system or on neurotoxin exposure to primary neurons. However, these assay are less reliable and/or do not take into account all of the desired neurotoxin functions. Thus, at present, the LD50 bioassay described above is the only reliable assay which is described in the monograph for BoNT/A in the European pharmacopeia. However, there is a need for a reliable assay for measuring neurotoxin activity which avoids the drawbacks of the LD50 bioassay.

Therefore, the technical problem underlying the present invention could be seen in the provision of means and methods for complying with the aforementioned needs. The technical problem is solved by the embodiments characterized in the claims and herein described below.

Thus, the present invention relates to a polypeptide having caspase activity comprising a large subunit and a small subunit wherein said caspase further comprises a neurotoxin cleavage site which upon cleavage activates the caspase activity.

The term "polypeptide having caspase activity" as used herein refers to a polypeptide which has a cysteine protease activity and in particular a cysteine-dependent aspartate-directed protease activity. Polypeptides having caspase activity (or so-called "caspases") are involved in cells in the programmed cell death (apoptosis) which occurs in many pathological and physiological processes including development. In a cellular context, caspases are arranged to operate in cascades. Accordingly, there are cascades which are activated by an external or internal stimulus (the so-called initiator or apical caspases). These initiator caspases subsequently activate further caspases by proteolytic cleavage (the so-called effector or executioner caspases). The effector caspases will than cleave other polypeptide substrates thererby triggering the apoptotic cell death in a cell. Initiator caspases are caspase 2, caspase 8, caspase 9 and caspase 10. Effector caspases are caspase 3, caspase 6 and caspase 7. The caspases caspase 4, caspase 5 and caspase 14 are enzymes which are involved in immunological processes and have not been characterized as initiator or effector caspases, respectively. Amino acid sequences encoding the aforementioned caspases are well known in the art (Yuan 1992, Development 116(2): 309-320; Ellis 1991, Annu Rev Cell Biol 7: 663-698; Yuan 1993, Cell 75(4): 641-652; Miura 1993, Cell 75(4): 653-660; Fuentes-Prior 2004, Biochem J 384: 201-232). In an aspect, human caspase 9 comprises an amino acid sequence as shown in SEQ ID NO: 6, human caspase 3 comprises an amino acid sequence as shown in SEQ ID NO: 7, human caspase 8 comprises an amino acid sequence as shown in SEQ ID NO: 8, human caspase 10 comprises an amino acid sequence as shown in SEQ ID NO: 9, human caspase 2 comprises an amino acid sequence as shown in SEQ ID NO: 10, human caspase 7 comprises an amino acid sequence as shown in SEQ ID NO: 11, and/or human caspase 6 comprises an amino acid sequence as shown in SEQ ID NO: 12.

Caspases as used herein also include polypeptides having caspase activity which have a variant amino acid sequence with respect to the aforementioned specific sequences shown in any one of SEQ ID NOs: 6 to 12. Said variant sequences comprise one or more amino acid substitutions, deletions and/or additions with respect to the specific sequences shown in any one of SEQ ID NOs: 6 to 12 referred to before. Moreover, such a variant polypeptide shall, in another aspect, comprise an amino acid sequence being at least 40%, at least 50%, at least 60%, at least 70%, at least 75%, at least 80%, at least 85%, at least 90%, at least 95%, at least 98% or at least 99% identical to the aforementioned specific amino acid sequence shown in any one of SEQ ID NOs: 6 to 12. The term "identical" as used herein refers to sequence identity characterized by determining the number of identical amino acids between sequences wherein the sequences are aligned so that the highest order match is obtained. It can be calculated using published techniques or methods codified in computer programs such as, for example, BLASTP or FASTA (Altschul 1990, J Mol Biol 215, 403). The percent identity values are, in one aspect, calculated over the entire amino acid sequence or over a sequence stretch of at least 50% of the query sequence. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (Higgins 1989, CABIOS 5, 151) or the programs Gap and BestFit (Needleman 1970, J Mol Biol 48; 443; Smith 1981, Adv Appl Math 2, 482), which are part of the GCG software packet (Genetics Computer Group 1991, 575 Science Drive, Madison, Wis., USA 53711), may be used. The sequence identity values recited above in percent (%) are to be determined, in another aspect of the invention, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

The caspases are expressed as inactive proenzymes (zymogens) consisting from the N-terminus to the C-terminus of (i) a prodomain, (ii) a small subunit and (iii) a large subunit. The prodomain of the initiator caspases contains interaction domains such as a CARD domain in caspases-2 and -9 or the death effector domain (DED) in caspases-8 and -10. These interaction domains enable the caspases to interact with polypeptides which initiate their activation. Some of these polypeptides which initiate the activation of the initiator caspase are, e.g., death receptors like Fas, TRAIL receptors and TNF receptor which can activate caspase-8 and -10. Substrates of the effector caspases on the other end of the caspase cascade are, e.g., nuclear lamins, ICAD/DFF45 (inhibitor of caspase activated DNase or DNA fragmentation factor 45), PARP (poly-ADP ribose polymerase) or PAK2 (P 21-activated kinase 2).

Accordingly, in an aspect, effector caspase activity can be measured by cleavage of one or more of the aforementioned substrates including cell cycle proteins, DNA repair proteins, signaling molecules, cytoskeletal proteins and others. In an aspect, the effector caspase activity is measured by determining PARP cleavage. PARP comprises a DEVD motif which is recognized and cleaved by the effector caspase caspase 3. For measuring PARP cleavage several protease activity assays are commercially available.

Alternatively and in another aspect, caspase activity of an effector caspase can be determined by determining the amount of cell death which occurs in a cell population such as a cell culture. Apoptotic cell death can be measured by various well known techniques. In an aspect, DNA fragmentation is determined which typically occurs as so-called apoptotic laddering and is caused by regular cleavage of the genomic DNA in a cell which undergoes apoptosis. In another aspect, blebbing can be analyzed via imaging methods using a specific dye such as Höchst 33258. Moreover, and in a further aspect, the phospholipid distribution can be determined and, in an aspect, the phosphatidylserin distribution. The phosphatidylserin distribution can be determined by a phosphatidylserin binding protein such as annexin V. Imaging platforms for measuring apoptosis based on annexin V have been recently reported and are described in Tait 2008, J Nuclear Medicine 49(10): 1573-76; Jeppsen 2008, J Biol Chem 283: 6126-35; Tait 2006, J Nuclear Medicine 47: 1546-53. It will be understood that the aforementioned measures for determining apoptosis can also be combined.

The caspase activity of an initiator caspase can be determined, in an aspect, as described for the effector caspase activity in an in vivo system like a cell culture or an in vitro (i.e. cell-free) system comprising also effector caspases. Moreover, the initiator caspase activity, in an aspect, can be determined based on the cleavage of effector caspases as substrate of the said initiator caspases.

The caspase activity, in an aspect, can be determined in a cell-free in vitro system as set forth above. Such a cell free system may be a cellular fraction which comprises the substrates of the caspase. Alternatively, an artificial solution can be applied comprising said substrates and which provides conditions under which caspases are active. In another aspect, the caspase activity can be determined in vivo in a suitable host cell which expresses the polypeptide of the present invention and which further comprises a biologically active neurotoxin polypeptide capable of cleaving the said polypeptide. As a result of the cleavage, the polypeptide of the present invention shall become activated and elicits apoptosis in the host cell. In an aspect, such an activity assay is also described in accordance with the method of the present invention elsewhere herein.

The term "neurotoxin cleavage site" as used herein refers to cleavage site which is recognized and cleaved by the endogenous protease of a neurotoxin polypeptide. Cleavage site which are recognized by the neurotoxin proteases are well known in the art (see, e.g., EP 1 926 744 B1). In principle, a neurotoxin cleavage site can be a cleavage site which naturally occurs in a substrate or which is an artificially designed cleavage site recognized and cleaved by the neurotoxin polypeptides protease. It will be understood that the properties of the neurotoxin cleavage site govern the kind of neurotoxin which can activate the polypeptide of the present invention. Neurotoxin polypeptides referred to herein, in an aspect, encompass BoNT/A, BoNT/B, BoNT/C1, BoNT/D, BoNT/E, BoNT/G, BoNT/F or TeNT all of which are well known in the art. For example, if a neurotoxin cleavage site is used which is specifically recognized and cleaved by BoNT/A, only the BoNT/A protease will be capable of activating the polypeptide of the present invention and, in particular, its caspase activity, whereas if a neurotoxin cleavage site is used which is specifically recognized and cleaved by BoNT/E, only the BoNT/E protease will be capable of activating the polypeptide of the present invention and, in particular, its caspase activity. In an aspect of the invention, the neurotoxin cleavage site is cleaved by mature BoNTs. In yet another aspect, it is cleaved by muteins of BoNTs, in an aspect, by muteins comprising or consisting of the BoNT light chain exhibiting the BoNT protease activity.

A neurotoxin cleavage site recognized and cleaved by the BoNT/A protease, in an aspect of the invention, is derived from a protein that is sensitive to cleavage by BoNT/A. In an aspect, such a protein is human SNAP25A or B or a homolog, paralog or ortholog thereof from rat, mouse, bovine, *Danio, Carassius, Xenopus, Torpedo, Strongylocentrotus, Loligo, Lymnaea* or *Aplysia*. Suitable cleavage sites derived from said proteins are disclosed in EP 1 926 744 B1.

A neurotoxin cleavage site recognized and cleaved by the BoNT/B protease, in an aspect of the invention, is derived from a protein that is sensitive to cleavage by BoNT/B. In an aspect, such a protein is human or mouse VAMP-1, VAMP-2 and VAMP-3/cellubrevin, bovine VAMP-2, rat VAMP-2 or VAMP-3, chicken VAMP-1, VAMP-2 or VAMP-3, *Torpedo* VAMP-1, *Strongylocentrotus* VAMP, *Drosophila* sybA, synB, synC, synD, or syn, *Hirudo* VAMP, *Xenopus* VAMP-2 or VAMP-3, *Danio* VAMP-1 or VAMP-2, *Loligo* VAMP, *Lymnaea* VAMP, *Aplysia* VAMP or *Caenorhabditis* SNB1-like or any ortholog, paralog or homolog thereof. Suitable cleavage sites derived from said proteins are disclosed in EP 1 926 744 B1.

A neurotoxin cleavage site recognized and cleaved by the BoNT/C1 protease, in an aspect of the invention, is derived from a protein that is sensitive to cleavage by BoNT/C1. In an aspect, such a protein is human and mouse Syntaxin 1A, Syntaxin 1B1, Syntaxin 2-1, Syntaxin 2-2, Syntaxin 2-3, Syntaxin 3A or Syntaxin 1B2, bovine or rat Syntaxin 1A, Syntaxin 1B1 or Syntaxin 1B2, rat Syntaxin 2 or Rat syntaxin 3, mouse Syntaxin 1A, Syntaxin 1B1, Syntaxin 1B2, Syntaxin 2, Syntaxin 3A, Syntaxin 3B or Syntaxin 3C, chicken Syntaxin 1A or Syntaxin 2; *Xenopus* Syntaxin 1A or Syntaxin 1B, *Danio* Syntaxin 1A, Syntaxin 1B or Syntaxin 3, *Torpedo* Syntaxin 1A or Syntaxin 1B, *Strongylocentrotus* Syntaxin 1A or Syntaxin 1B, *Drosophila* Syntaxin 1A or Syntaxin 1B, *Hirudo* Syntaxin 1A or Syntaxin 1B, *Loligo* Syntaxin 1A or Syntaxin 1B, *Lymnaea* Syntaxin 1A or Syntaxin 1B or any ortholog, paralog or homolog thereof. Suitable cleavage sites derived from said proteins are disclosed in EP 1 926 744 B1.

A neurotoxin cleavage site recognized and cleaved by the BoNT/D protease, in an aspect of the invention, is derived from a protein that is sensitive to cleavage by BoNT/D. In an aspect, such a protein is human or mouse VAMP-1, VAMP-2 and VAMP-3/cellubrevin, bovine VAMP-2, rat VAMP-2 or VAMP-3, chicken VAMP-1, VAMP-2 or VAMP-3, *Torpedo* VAMP-1, *Strongylocentrotus* VAMP, *Drosophila* sybA, synB, synC, synD, or syn, *Hirudo* VAMP, *Xenopus* VAMP-2 or VAMP-3, *Danio* VAMP-1 or VAMP-2, *Loligo* VAMP, *Lymnaea* VAMP, *Aplysia* VAMP or *Caenorhabditis* SNB1-like or any ortholog, paralog or homolog thereof. Suitable cleavage sites derived from said proteins are disclosed in EP 1 926 744 B1.

A neurotoxin cleavage site recognized and cleaved by the BoNT/E protease, in an aspect of the invention, is derived from a protein that is sensitive to cleavage by BoNT/E. In an aspect, such a protein is, such a protein is human SNAP-25A or B or a homolog, paralog or ortholog thereof from rat, mouse, bovine, *Danio, Carassius, Xenopus, Torpedo, Strongylocentrotus, Loligo, Lymnaea* or *Aplysia*. Suitable cleavage sites derived from said proteins are disclosed in EP 1 926 744 B1.

A neurotoxin cleavage site recognized and cleaved by the BoNT/F protease, in an aspect of the invention, is derived from a protein that is sensitive to cleavage by BoNT/F. In an aspect, such a protein is human or mouse VAMP-1, VAMP-2 and VAMP-3/cellubrevin, bovine VAMP-2, rat VAMP-2 or VAMP-3, chicken VAMP-1, VAMP-2 or VAMP-3, *Torpedo* VAMP-1, *Strongylocentrotus* VAMP, *Drosophila* sybA, synB, synC, synD, or syn, *Hirudo* VAMP, *Xenopus* VAMP-2 or VAMP-3, *Danio* VAMP-1 or VAMP-2, *Loligo* VAMP, *Lymnaea* VAMP, *Aplysia* VAMP or *Caenorhabditis* SNB1-like or any ortholog, paralog or homolog thereof. Suitable cleavage sites derived from said proteins are disclosed in EP 1 926 744 B1.

A neurotoxin cleavage site recognized and cleaved by the BoNT/G protease, in an aspect of the invention, is derived from a protein that is sensitive to cleavage by BoNT/G. In an aspect, such a protein is, such a protein is human or mouse VAMP-1, VAMP-2 and VAMP-3/cellubrevin, bovine VAMP-2, rat VAMP-2 or VAMP-3, chicken VAMP-1, VAMP-2 or VAMP-3, *Torpedo* VAMP-1, *Strongylocentrotus* VAMP, *Drosophila* sybA, synB, synC, synD, or syn, *Hirudo* VAMP, *Xenopus* VAMP-2 or VAMP-3, *Danio* VAMP-1 or VAMP-2, *Loligo* VAMP, *Lymnaea* VAMP, *Aplysia* VAMP or *Caenorhabditis* SNB1-like or any ortholog, paralog or homolog thereof. Suitable cleavage sites derived from said proteins are disclosed in EP 1 926 744 B1.

A neurotoxin cleavage site recognized and cleaved by the TeNT protease, in an aspect of the invention, is derived from a protein that is sensitive to cleavage by TeNT. In an aspect, such a protein is human or mouse VAMP-1, VAMP-2 and VAMP-3/cellubrevin, bovine VAMP-2, rat VAMP-2 or VAMP-3, chicken VAMP-1, VAMP-2 or VAMP-3, *Torpedo* VAMP-1, *Strongylocentrotus* VAMP, *Drosophila* sybA, synB, synC, synD, or syn, *Hirudo* VAMP, *Xenopus* VAMP-2 or VAMP-3, *Danio* VAMP-1 or VAMP-2, *Loligo* VAMP, *Lymnaea* VAMP, *Aplysia* VAMP or *Caenorhabditis* SNB1-like or any ortholog, paralog or homolog thereof. Suitable cleavage sites derived from said proteins are disclosed in EP 1 926 744 B1.

A neurotoxin cleavage site recognized and cleaved by the BoNT proteases, in another aspect of the invention, is derived from the autocatalytic cleavage sites found in the BoNT proteins. In aspects, a neurotoxin cleavage site to be used in accordance with the present invention and which is derived from the autocatalytic cleavage site of a given BoNT or TeNT comprises at least 6, at least 8, at least 10 or at least 15 consecutive residues of including the BoNT/A residues 250Tyr-251Tyr, the BoNT/B residues 256Phe-257Phe, the BoNT/C1 residues 257Phe-258Tyr, the BoNT/D residues 257Phe-258Phe, the BoNT/E residues 239Pro-240Leu, the BoNT/F residues 254Pro-255Leu, the BoNT/G residues 256Phe-257Phe, the TeNT residues 259Ile-260Tyr, the BoNT/A residues Phe266-Gly267, the BoNT/B residues Phe272-Gly273, the BoNT/C1 residues Phe273-Gly274, the BoNT/D residues Phe273-Gly274, the BoNT/E residues Phe255-Gly256, the BoNT/F residues Phe270-Gly271, the BoNT/G residues Phe272-Gly273 or the TeNT residues Phe275-Gly276. Suitable cleavage sites derived from said BoNTs and TeNT are disclosed in EP 1 926 744 B1.

In an aspect of the polypeptide of the present invention, said neurotoxin cleavage site is a cleavage site recognized and cleaved by the BoNT/A protease. In an aspect, said cleavage site is shown in any one of SEQ ID NO: 1 to 5.

In a further aspect of the polypeptide of the present invention, said neurotoxin cleavage site is a cleavage site recognized and cleaved by the BoNT/B, BoNT/C1, BoNT/D, BoNT/E, BoNT/F, BoNT/G or TeNT protease.

In an aspect of the polypeptide of the present invention, said neurotoxin cleavage site is located between the C-terminal proximal region of the large subunit and the N-terminal proximal region of the small subunit. In a further aspect, said C-terminal proximal region of the large subunit consists the amino acids corresponding to amino acids C170 to D175, L168 to E173, Q161 to D175, or Q161 to E173 of the large subunit of caspase 3 and said N-terminal proximal region of the small subunit consists of the amino acids corresponding to amino acids S176 to V190 or S176 to C184 of the small subunit of caspase 3. In a further aspect, said C-terminal proximal region of the large subunit consists the amino acids corresponding to amino acids V174 to D179, H172 to V177, Q165 to D179, or Q165 to V177 of the large subunit of caspase 6 and said N-terminal proximal region of the small subunit consists of the amino acids corresponding to amino acids S180 to A194 or S180 to V188 of the small subunit of caspase 6. In a further aspect, said C-terminal proximal region of the large subunit consists the amino acids corresponding to amino acids D193 to D198, L191 to Q196, Q184 to D198, or Q184 to Q196 of the large subunit of caspase 7 and said N-terminal proximal region of the small subunit consists of the amino acids corresponding to amino acids S199 to V213 or S199 to R207 of the small subunit of caspase 7. In a further aspect, said C-terminal proximal region of the large subunit consists the amino acids corresponding to amino acids K369 to D374, Y367 to E372, Q360 to D374, or Q360 to E372 of the large subunit of caspase 8 and said N-terminal proximal region of the small subunit consists of the amino acids corresponding to amino acids S375 to D389 or S375 to T383 of the small subunit of caspase 8. In a further aspect, said C-terminal proximal region of the large subunit consists the amino acids corresponding to amino acids P367 to D372, 1365 to E370, Q358 to D372, or Q358 to E370 of the large subunit of caspase 10 and said N-terminal proximal region of the small subunit consists of the amino acids corresponding to amino acids A373 to A386 or A373 to Q380 of the small subunit of caspase 10. In a further aspect, said C-terminal proximal region of the large subunit consists the amino acids corresponding to amino acids H310 to D315, K308 to E313, Q301 to D315, or Q301 to E313 of the large subunit of caspase 9 and said N-terminal proximal region of the small subunit consists of the amino acids corresponding to amino acids A316 to T330 or A316 to I324 of the small subunit of caspase 9. In a further aspect, said C-terminal proximal region of the large subunit consists the amino acids corresponding to amino acids R311 to D316, T309 to Q314, Q302 to D316, or Q302 to Q314 of the large subunit of caspase 2 and said N-terminal proximal region of the small subunit consists of the amino acids corresponding to amino acids G317 to T331 or G317 to K325 of the small subunit of caspase 2.

In another aspect of the polypeptide of the present invention, said polypeptide further comprises a prodomain. In an aspect, the prodomain comprises amino acids 1 to 29 of caspase 3, amino acid 1 to 24 of caspase 7, amino acids 1 to 24 of caspase 6, amino acids 1 to 217 of caspase 8, amino acids 1 to 226 of caspase 10, amino acids 1 to 139 of caspase 9 or amino acids 1 to 153 of caspase 2. In an aspect, said neurotoxin cleavage site is located between the C-terminal proximal region of the prodomain and the N-terminal proximal region of the large subunit. In a further aspect, the said C-terminal proximal region of the prodomain consists of the amino acids corresponding to amino acids S29 to D34 of the large subunit of caspase 3 and said N-terminal proximal region of the large domain consists of the amino acids corresponding to amino acids N35 to D40 of the large subunit of caspase 3. In an aspect, the C-terminal proximal region of the prodomain for caspase 3, thus, encompasses amino acids 29 to 34 and the N-terminal proximal region of the large domain consists the amino acids 35 to 40, the C-terminal proximal region of the prodomain for caspase 6 encompasses amino acids 24 to 29 and the N-terminal proximal region of the large domain consists the amino acids 30 to 35, the C-terminal proximal region of the prodomain for caspase 7 encompasses amino acids 24 to 29 and the N-terminal proximal region of the large domain consists the amino acids 30 to 35, the C-terminal proximal region of the prodomain for caspase 8 encompasses amino acids 217 to 222 and the N-terminal proximal region of the large domain consists the amino acids 223 to 228, the C-terminal proximal region of the prodomain for caspase 9 encompasses amino acids 153 to 158 and the N-terminal proximal region of the large domain consists the amino acids 159 to 164, the C-terminal proximal region of the prodomain for caspase 10 encompasses amino acids 231 to 236 and the N-terminal proximal region of the large domain consists the amino acids 237 to 242.

As discussed elsewhere herein, in another aspect of the polypeptide of the present invention, said polypeptide is an effector caspase. In an aspect, said effector caspase is selected from the group consisting of: caspase 3, caspase 6 and caspase 7.

In another aspect, the caspase from which the polypeptide of the present invention is derived by introducing a neurotoxin cleavage site is caspase 3.

In an further aspect, the polypeptide of the present invention comprises an amino acid sequence as shown in any one of SEQ ID NOs: 6 to 10 or is a variant thereof as described elsewhere herein retaining caspase activity and the neurotoxin cleavage site which upon cleavage activates the caspase activitiy.

As discussed also elsewhere herein, in a further aspect of the polypeptide of the present invention, said polypeptide is an initiator caspase. In an aspect, said initiator caspase is selected from the group consisting of: caspase 2, caspase 8, caspase 9 and caspase 10.

The present invention further contemplates a polynucleotide encoding the polypeptide of the present invention.

The term "polynucleotide" as used herein refers to single- or double-stranded DNA molecules as well as to RNA molecules. Encompassed by the said term is genomic DNA, cDNA, hnRNA, mRNA as well as all naturally occurring or artificially modified derivatives of such molecular species. The polynucleotide may be in an aspect a linear or circular molecule. Moreover, in addition to the nucleic acid sequences encoding the polypeptide of the present invention, a polynucleotide of the present invention may comprise additional sequences required for proper transcription and/or translation such as 5'- or 3'-UTR sequences. The nucleic acid sequences encoding the polypeptide of the present invention can be derived from the polypeptide sequences by a skilled artisan without further ado. In light of the degeneracy of the genetic code, optimized codons may be used in the nucleic acid sequences encoding the polypeptide of the present invention in the polynucleotide. Thereby, optimal expression in, e.g., a host cell of the present invention can be achieved.

The present invention furthermore pertains to a vector comprising the polynucleotide of the present invention.

The term "vector", preferably, encompasses phage, plasmid, viral or retroviral vectors as well as artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homologous or heterologous recombination as described in detail below. The vector encompassing the polynucleotides of the present invention, in an aspect, further comprises selectable markers for propagation and/or selection in a host cell. The vector may be incorporated into a host cell by various techniques well known in the art. For example, a plasmid vector can be introduced in a precipitate such as a calcium phosphate precipitate or rubidium chloride precipitate, or in a complex with a charged lipid or in carbon-based clusters, such as fullerens. Alternatively, a plasmid vector may be introduced by heat shock or electroporation techniques. Should the vector be a virus, it may be packaged in vitro using an appropriate packaging cell line prior to application to host cells. Retroviral vectors may be replication competent or replication defective. In the latter case, viral propagation generally will occur only in complementing host/cells. Moreover, in an aspect of the invention, the polynucleotide is operatively linked to expression control sequences allowing expression in prokaryotic or eukaryotic host cells or isolated fractions thereof in the said vector. Expression of the polynucleotide comprises transcription of the polynucleotide into a translatable mRNA. Regulatory elements ensuring expression in host cells are well known in the art. In an aspect, they comprise regulatory sequences ensuring initiation of transcription and/or poly-A signals ensuring termination of transcription and stabilization of the transcript. Additional regulatory elements may include transcriptional as well as translational enhancers. Possible regulatory elements permitting expression in prokaryotic host cells comprise, e.g., the lac-, trp- or tac-promoter in *E. coli*, and examples for regulatory elements permitting expression in eukaryotic host cells are the AOX1- or the GAL1-promoter in yeast or the CMV-, SV40-, RSV-promoter (Rous sarcoma virus), CMV-enhancer, SV40-enhancer or a globin intron in mammalian and other animal cells. Moreover, inducible expression control sequences may be used in an expression vector encompassed by the present invention. Such inducible vectors may comprise tet or lac operator sequences or sequences inducible by heat shock or other environmental factors. Suitable expression control sequences are well known in the art. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pBluescript (Stratagene), pCDM8, pRc/CMV, pcDNA1, pcDNA3 (Invitrogen) or pSPORT1 (Invitrogen). Preferably, said vector is an expression vector and a gene transfer or targeting vector. Expression vectors derived from viruses such as retroviruses, vaccinia virus, adeno-associated virus, herpes viruses, or bovine papilloma virus, may be used for delivery of the polynucleotide or vector of the invention into a targeted cell population. Such approaches can also be used for gene therapy. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994).

Moreover, encompassed by the present invention is a host cell comprising the polypeptide, the polynucleotide or the vector of the present invention.

The term "host cell" as used herein as used herein encompasses prokaryotic and eukaryotic host cells. In an aspect the host cell is a bacterial cell. In one aspect, the said bacterial host cell is an *E. coli* host cell or a clostridial host cell, in an aspect a *clostridium botulinum* host cell. Such a bacterial host cell may be used, e.g., for reproduction of the polynucleotide or the vector of the present invention. A eukaryotic host cell, in an aspect, is a cell which comprises the polypeptide and either the polynucleotide or the vector of the present invention wherein said polynucleotide or vector are expressed in the host cell in order to generate the polypeptide. In an aspect, the eukaryotic host cell may be a cell of a eukaryotic host cell line which stably expresses the polynucleotide of the invention. In another aspect, the host cell is a eukaryotic host cell which has been transiently transfected with the polynucleotide or vector of the invention and which expresses the polynucleotide of the invention. A host cell according to the present invention, in an aspect, further comprises substrates for the caspase activity of the polypeptide of the invention. Moreover, in another aspect, the host cell is capable of responding to the caspase activity conferred by the cleaved polypeptide of the present invention by a change of the cellular physiology, in an aspect by apoptotic cell death or by at least the activation of a cascade which is capable of inducing apoptosis. In an aspect, said change of cellular physiology can be detected by a change of cellular morphology, by DNA degradation, in aspect apoptotic laddering, and/or by cleavage of substrates of the apoptotic caspase cascade including nuclear lamins, ICAD/DFF45 (inhibitor of caspase activated DNase or DNA fragmentation factor 45), PARP (poly-ADP ribose polymerase) or PAK2 (P 21-activated kinase 2). In an aspect the host cell is a eukaryotic host cell, in another aspect a mammalian host cell and in yet another aspect a cell which is capable of uptaking neurotoxin polypeptides. In an aspect, a cell capable of uptaking neurotoxin polypeptides can be a cell produces endogenously all necessary components for the neurotoxin polypeptde uptake. In an aspect, the cel is a neuronal cell. In another aspect, a cell capable of uptaking neurotoxin polypeptides is a cell which has been genetically engineered to produce the components necessary for the neurotoxin polypeptide uptake. How such cells can be genetically engineered by molecular biology techniques is well known to the skilled person.

In an aspect of the host cell of the present invention, said host cell is selected from the group consisting of: primary neuronal cells, cell line N1E-11, cell line Neuro2a, cell line PC12, and cell line SH-SY5Y.

The present invention relates to a method for determining neurotoxin activity in a sample comprising the steps of:
  (a) contacting the polypeptide of the present invention with a sample suspected to comprise neurotoxin activity; and
  (b) measuring caspase activity of the polypeptide, whereby neurotoxin activity in the sample is determined.

The method of the present invention can be assisted by automation. Specifically, in an aspect, step a) and/or b) may be assisted by robotic devices and automated systems for measuring the caspase activity. Suitable systems are known in the art and depend on the type of response to be determined. Moreover, the method may comprise additional steps pertaining to the sample preparation or generation of the polypeptide of the present invention.

The term "contacting" as used herein refers to bringing at least two different compounds in physical proximity as to allow physical and/or chemical interaction of said compounds. In the aforementioned method, the polypeptide according to the present invention is contacted with a sample suspected to comprise a biologically active neurotoxin polypeptide. The polypeptide shall be contacted for a time and under conditions sufficient to allow cleavage of the neurotoxin cleavage site in the polypeptide of the present invention by the neurotoxin polypeptide comprised by the sample. Contacting as used herein, in an aspect occurs in a host cell of the present invention containing the polypeptide of the present invention. Thus, in an aspect, said polypeptide is comprised by a host cell and, in an aspect, the host cell of the present invention. The said time and conditions will dependent on the amount of neurotoxin polypeptide comprised by the sample as well as on the uptake of the neurotoxin polypeptide by the host cell. The person skilled in the art is well aware of which conditions need to be applied dependent on the host cell, kind of sample, and kind of neurotoxin which shall be determined. In another aspect, contacting occurs in a cell free system comprising the polypeptide of the invention as well as a substrate of the polypeptide of the present invention and/or other caspases. Th cell free system shall allow for measuring the activity of the polypeptide of the present invention upon contacting the system with a sample and, thus, allows for determining the neurotoxin activity in said sample.

The term "sample" refers to a sample suspected to comprise neurotoxin polypeptide. The sample, in an aspect, is an aqueous solution. Such a sample may be a biological sample or may be a sample of an artificially generated aqueous solution. Such solutions, in an aspect, are obtained at different stages during neurotoxin manufacture, either for quality control and/or activity determination/specification purposes or for safety control. It is envisaged that the neurotoxin present in the said sample shall exhibit at least the neurotoxin protease activity. In another aspect, the neurotoxin is fully biologically active. In an aspect the said fully biologically active neurotoxin is required for entering the cell and for activating the read out based on the caspase polypeptide of the present invention. Accordingly, such a fully biologically active neurotoxin is to be applied if a host cell is to be contacted with the sample to be analyzed by the method of the invention. In another aspect, the sample to be applied for the method of the invention comprises neurotoxin polypeptides or fragments thereof which merely exhibit neurotoxin protease activity. Such neurotoxin polypeptides or fragments are, in an aspect, muteins of neurotoxin polypeptides comprising or consisting essentially of a proteolytically active light chain. It is to be understood that samples comprising neurotoxin polypeptides or fragments thereof which merely exhibit neurotoxin protease activity shall be used if the sample is to be contacted to a cell free system as specified elsewhere herein in detail.

The caspase activity is measured by determining cleavage of a substrate of the caspase activity conferred by the polypeptide of the present invention. The substrate cleavage can be measured, in an aspect, by determining the cleaved substrate directly. In a further aspect, the cleavage of the substrate is determined by PAGE-based techniques, by immunofluorescent-based techniques such as FRET or flow cytometry, by antibody-based techniques such as Western blotting or ELISA, by size exclusion chromatography, HPLC coupled to a suitable detector, or by spectroscopic techniques such as mass spectroscopy or NMR spectroscopy. In another aspect, the caspase activity is determined indirectly, i.e. by determining a process downstream of the cleavage of the substrate. Since the caspase cascade activated by the polypeptide of the present invention in a host cell, in an aspect, results is apoptosis, its activity results in detectable changes of the cellular physiology and, finally, in apoptotic cell death. A change of the cellular physiology can be detected by a change of cellular morphology, by DNA fragmentation, in aspect apoptotic laddering, and/or by cleavage of substrates of the apoptotic caspase cascade including cell cycle proteins, DNA repair proteins, signaling molecules, cytoskeletal proteins and others. In an aspect, the substrate is one or more of the following substrates: nuclear lamins, ICAD/DFF45 (inhibitor of caspase activated DNase or DNA fragmentation factor 45), PARP (poly-ADP ribose polymerase) or PAK2 (P 21-activated kinase 2).

The amount of neurotoxin polypeptide in a sample can be determined quantitatively or qualitatively. For a quantitative detection, in an aspect, the measured amount can be compared to a calibration curve which is to be established by subjecting calibration samples having predetermined amounts of the neurotoxin polypeptide to be determined in the method of the present invention.

In an aspect of the method of the present invention, said caspase activity is measured by determining cleavage of at least one substrate of the polypeptide in vivo or in vitro. In an aspect, said substrate is at least one effector caspase. The cleavage of an effector caspase as substrate can be achieved by using an initiator caspase activity in the polypeptide of the present invention. The cleavage of an effector caspase as substrate by the polypeptide of the present invention, in an aspect, results in an amplification of the original caspase activity. Accordingly, such a polypeptide of the present invention has a high sensitivity also for low amounts of neurotoxin polypeptide.

Specifically, it is envisaged in the method of the present invention to measure the caspase activity by determining apoptosis in a host cell culture comprising host cells expressing the polypeptide of the present invention having caspase activity. A host cell culture to be used in this context may be a neuronal host cell culture comprising neuronal cells which are capable to take up the neurotoxin polypeptide properly. To this end, the caspase activity of the polypeptide of the present invention will be activated after the host cell in the host cell culture has been contacted to a neurotoxin polypeptide containing sample. The neurotoxin containing sample can be derived either from medicament comprising the neurotoxin polypeptide or a cellular extract from Botulinum bacteria or host cells which are genetically engineered to express a neurotoxin polypeptide and which are used for the production of such a medicament. The biologically active neurotoxin of the sample will enter the said host cell and will subsequently activate the polypeptide of the invention comprising the respective cleavage site for the neurotoxin protease. The activated polypeptide of the invention having caspase activity will than activate the caspase cascade and, thus, will induce apoptosis in the host cell. Apoptosis of the host cell can then be measured as described in detail elsewhere herein. Specifically, apoptosis is measured by determining cellular and subcellular morphology of the cells by imaging techniques including the determination of blebbing using the dye Höchst 33258.

As will be understood from the above, the present invention in general relates to the use of the polypeptide, the polynucleotide, the vector or the host cell of the present invention for determining neurotoxin activity in a sample.

Furthermore, a kit for determining neurotoxin activity is provided in accordance with the present invention. Said kit comprises the polypeptide, the polynucleotide, the vector or the host cell of the present invention.

The term "kit" as used herein refers to a collection of means comprising the polypeptide, the polynucleotide, the vector and/or the host cell of the present invention which are provided in separate or common vials in a ready to use manner for carrying out the method of the present invention. In an aspect, the kit comprises additional means for carrying out the method of the present invention, in an aspect, calibration standard solutions comprising neurotoxin polypeptide and/or means for measuring the caspase activity such as detection agents for determining cleavage of caspase substrates or agents for determining apoptosis in a cell. Furthermore, in an aspect, the kit comprises instructions for carrying out the method of the present invention. These instructions can be provided as a manual or can be in the form of an computer-implementable algorithm on a data storage medium which upon implementation is capable of governing one or more steps of the method of the invention.

All references cited in this specification are herewith incorporated by reference with respect to their entire disclosure content and the disclosure content specifically mentioned in this specification.

FIGURES

FIG. 1: Caspases are costitutively expressed as enzymatically in inactive zymogens. In case of Caspase 3, pro-Caspase-3 is a 32 kDa protein, which undergoes cleavage by initiator caspases Caspases 8 or 9 and autoprocessing into a larger and a smaller fragment or 17 and 12 kDa size. They form the enzymatically active heterodimer/tetramer which cleaves with some preference after DEVD sequence motifs. A typical substrate would be PARP which is cleaved into a 85 kDa fragment and minor fragments and is inactivated. Active caspase-3 cleaves a large number of substrates and can be inhibited with small peptides using this sequence preference linked to alkylating structures such as zDEVD-fluoromethylketon. A SNAP25 sequence recognized and cleaved by BoNT/A, C or E or BoNT with mutated sequences is inserted between the prodomain and the large subunit or, between the large and the small subunit in order to allow BoNT/A, C or E or BoNT with mutated sequences to activate caspase 3 by cleavage at this site.

FIG. 2: Test-expression of pTZE02/Casp3.1 in different *E. coli* expression strains SDS-PAGE analysis. Gel 12%, stained with Coomassie Blue. Selected marker sizes are depicted to the left. To clearly relate bands in the Coomassie stained gel to the Casp 3.1 target and estimate the amount of soluble compared to insoluble target, western blot analysis with anti-Strep-Tag antibody was performed.

FIG. 3: Test-expression of pTZE02/Casp3.1 in different *E. coli* expression strains Western-blot analysis. Gel 12%, detection with anti Strep antibody. Selected marker sizes are depicted to the left. The western-blot analysis revealed the presence of a protein running between the 25 and the 35 kDa molecular weight marker band in the soluble and the insoluble protein fraction of all tested expression conditions. The BL21(DE3) as well as the BL21(DE3)/pGroESEL expression only showed a very weak signal detected in the soluble protein fraction with the Strep-Tag antibody. The detected protein band in the Rosetta(DE3)/pRARE2 and the Rosetta(DE3)/pLys expression corresponding with the expected molecular weight (30.4 kDa) of the translated Casp3.1 protein revealed, that at least 20-30% of the target should be present in a soluble form.

FIG. 4: Test-expression of pTZE44/Casp3.1 in different *E. coli* expression strains SDS-PAGE analysis. Gel 12%, stained with Coomassie Blue. Selected marker sizes are depicted to the left. To clearly identify MBP-Casp 3.1-fusion protein bands in the Coomassie stained gel and estimate the amount of soluble compared to insoluble target, western blot analysis was performed.

FIG. 5: Test-expression of pTZE44/Casp3.1 in different *E. coli* expression strains Western-blot analysis. Gel 12%, detection with anti Strep antibody. Selected marker sizes are depicted to the left.

FIG. 6: Test-expression of pTZE02/Casp3.1 in *E. coli* Rosetta(DE3)/pRARE2 SDS-PAGE analysis. Gel 12%, stained with Coomassie Blue. Selected marker sizes are depicted to the left.

FIG. 7: Test-expression of pTZE02/Casp3.1 in *E. coli* Rosetta(DE3)/pRARE2 Western-blot analysis. Gel 12%, detection with anti Strep antibody. Selected marker sizes are depicted to the left.

FIG. 8: Test-expression of pTZE02/Casp3.1 in *E. coli* Rosetta(DE3)/pLys SDS-PAGE analysis. Gel 12%, stained with Coomassie Blue. Selected marker sizes are depicted to the left.

FIG. 9: Test-expression of pTZE02/Casp3.1 in *E. coli* Rosetta(DE3)/pLys Western-blot analysis. Gel 12%, detection with anti Strep antibody. Selected marker sizes are depicted to the left.

FIG. 10: Test-expression of pTZP01/Casp3.1 in *P. pastoris* X33, KM71 and GS115 SDS-PAGE analysis. Gel 12%, stained with Coomassie Blue.

FIG. 11: Test-expression of pTZP01/Casp3.1 in *P. pastoris* X33, KM71 and GS115 Western-blot analysis. Gel 12%, detection with anti Strep antibody. Selected marker sizes are depicted to the left.

FIG. 12: Test-expression of pHILD2/Casp3.1 in *P. pastoris* KM71 and GS115 Left panel: SDS-PAGE analysis. Gel 12%, stained with Coomassie Blue. Right panel: Western-blot analysis. Gel 12%, detection with anti Strep antibody. Selected marker sizes are depicted to the left.

FIG. 13: SDS PAGE and Western blot analysis of cleavage reaction products induced by BoNT/A.

EXAMPLES

Example 1

Cloning of *E. coli* Constructs (pTZ_E02_Casp3.1 and pTZ_E44_Casp3.1)

This construct is a pET24d based vector derivative, the final construct encodes for Procaspase 3.1 with a C-terminal Streptag II. The following Cloning strategy was applied: Procaspase 3.1 was PCR-amplified from plasmid MRZ_Casp3.1 with the following primers:

```
1369_Casp3.1_BsmBI_fp
                                        (SEQ ID NO: 13)
AACGTCTCTGATGAACAGCTACAAGATGGACTACCC 1369_Casp3.1_2Stop_AscI_rp
                                        (SEQ ID NO: 14)
AAGGCGCGCCTATTATTTTTCGAACTGCGGGTGGCTC
```

Procaspase 3.1 was subcloned into pTZE02 using the restriction sites AscI/BsmBI. Positive clones were screened by PCR and plasmid DNA was isolated. The cloned target sequence of the final construct was verified via sequencing. The pTZ_E44_Casp3.1 construct consists of ssMBP (Maltose binding protein with signal sequence for periplasmatic expression) fused to Procaspase 3.1. The final construct encodes for a periplasmatic expressed MBP-Procaspase 3.1-fusionprotein with a C-terminal Streptag II. The MBP fusion partner can be cleaved from the Procaspase 3.1 part using the serin protease factor Xa yielding native, Strep-tagged Procaspase 3.1. The following Cloning strategy was applied: Procaspase 3.1 was PCR-amplified from plasmid MRZ_Casp3.1 with the following primers: 1369_Casp3.1_BsmBI_fp and 1369_Casp3.1__2Stop_AscI_rp. Procaspase 3.1 was subcloned into pTZE44 using the restriction sites AscI/BsmBI. Positive clones were screened by PCR and plasmid DNA was isolated. The cloned target sequence of the final construct was verified via sequencing.

Example 2

Cloning of *P. pastoris* Constructs pTZ_P01_Casp3.1 and pHIL-D2_Casp3.1

The pTZ_P01_Casp3.1 construct is a pPICZalphaA based vector derivative carrying a secretion signal (α-factor). The final construct will be secreted as Procaspase 3.1 with a C-terminal Streptag II. The following cloning strategy was applied: Procaspase 3.1 was PCR-amplified from plasmid MRZ_Casp3.1 with the following primers: 1369_Casp3.1_BsmBI_fp and 1369_Casp3.1__2Stop_AscI_rp. Procaspase 3.1 was subcloned into pTZP01 using the restriction sites AscI/BsmBI. Positive clones were screened by PCR and plasmid DNA was isolated. The cloned target sequence of the final construct was verified via sequencing. The pHIL-D2_Casp3.1 construct will be expressed intracellular as Procaspase 3.1 with an N-terminal 6×His-tag. The following cloning strategy was applied: Procaspase 3.1 was PCR-amplified from plasmid MRZ_Casp3.1 with the following primers:

```
1369_Casp3.1_pHILD2_fp
                                             (SEQ ID NO: 15)
AACAATTGTCTGCCATCATGCATCATCATCATCATCATAACAGCTACAAG

ATGGACTACC

1369_Casp3.1_pHILD2_rp
                                             (SEQ ID NO: 16)
AACAATTGTTATTAGAGACCGTGGTAGAAGTACAGCTC
```

Procaspase 3.1 was subcloned into pHILD2 using the restriction sites MfeI/EcoRI. The insertion can take place in two different orientations (cw and ccw). The desired orientation (1369_pHILD2_Casp3.1_cw) is identified by restriction analysis and sequencing. Positive clones were screened by PCR and plasmid DNA was isolated. The cloned target sequence of the final construct was verified via sequencing.

Example 3

Expression in *E. coli* of pTZE02/Casp3.1

The construct is a pET24d based vector derivative, encoding for Procaspase 3.1 with a Cterminal Streptag II. The expected molecular weight of Casp3.1 is 30.4 KDa, with an estimated pI of 8.5. For analyzing the expression pTZE02/Casp3.1 (KanR) was transformed into the following *E. coli* strains:
BL21 (DE3)
BL21 (DE3)/pGroEL ES (CamR)
Rosetta (DE3)/pRARE2 (CamR)
Rosetta (DE3)/pLys (CamR)

Figure 2:
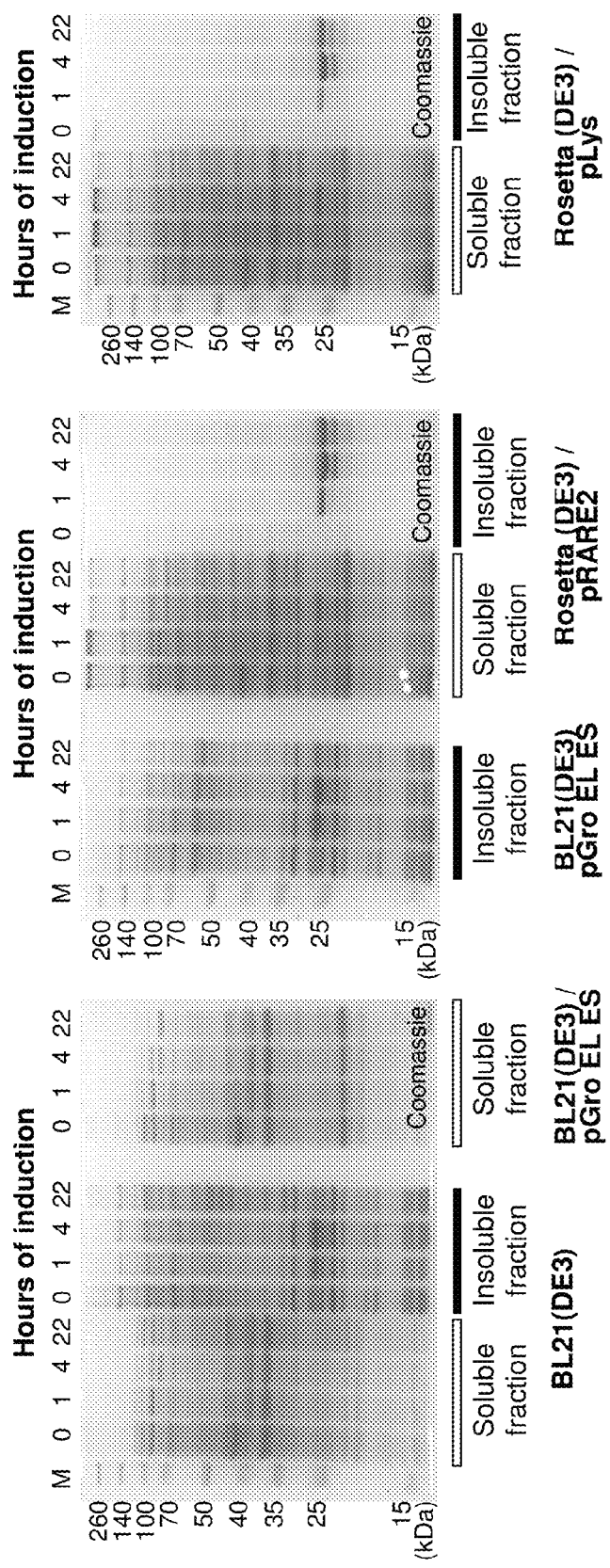
Figure 3:
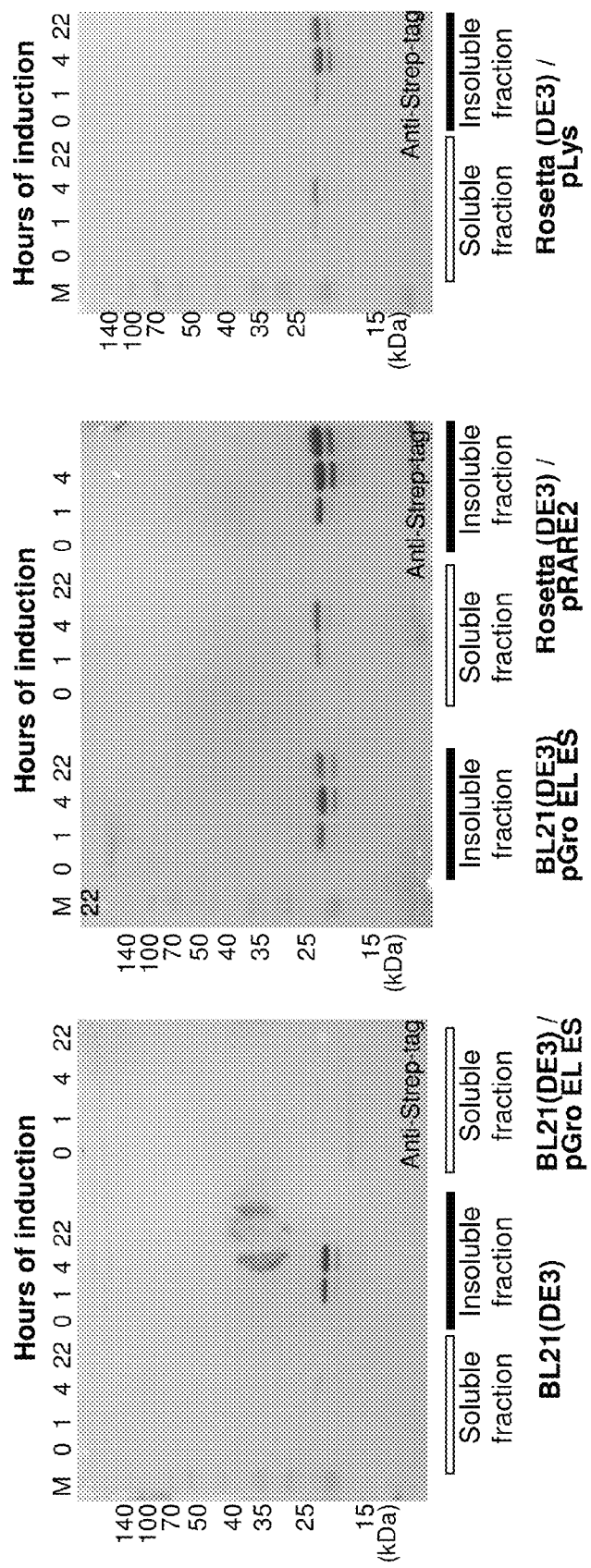

Cells were grown at 37° C. in LB medium supplemented with 50 µg/ml kanamycin (and 30 µg/ml chloramphenicol for the respective strains) until an OD600 of 0.4 was reached. Each culture was shifted to 30° C. and grown until an OD 600 of 0.5 was reached. Cultures were induced with 0.2 mM IPTG and grown for another 22 hours at 30° C. After 0, 1, 4 and 22 hours of induction samples were taken and treated with Bug buster HT solution (Novagen) to break the cells and separate soluble and insoluble protein fractions. Samples were analysed via SDS-PAGE analysis on 12% Gels (FIGS. 2 and 3).

Example 4

Expression in *E. coli* of pTZE44/Casp3.1

The construct consists of ssMBP (Maltose binding protein with signal sequence for periplasmatic expression) fused to Procaspase 3.1. The final construct encodes for a periplasmatic expressed MBP-Procaspase 3.1-fusionprotein with a C-terminal Streptag II. The MBP fusion partner can be cleaved from the Procaspase 3.1 part using the serin protease factor Xa yielding native, Strep-tagged Procaspase 3.1. The expected molecular weight of MBP-Casp3.-fusion protein (MBP-Signal sequence cleaved off) is 74 KDa, with an estimated pI of 6.9. For analyzing the expression pTZE44/Casp3.1 (AmpR) was transformed into the following *E. coli* strains:
BL21 (DE3)
BL21 (DE3)/pGroEL ES (CamR)
Rosetta (DE3)/pRARE2 (CamR)
Rosetta (DE3)/pLys (CamR)

Figure 4:
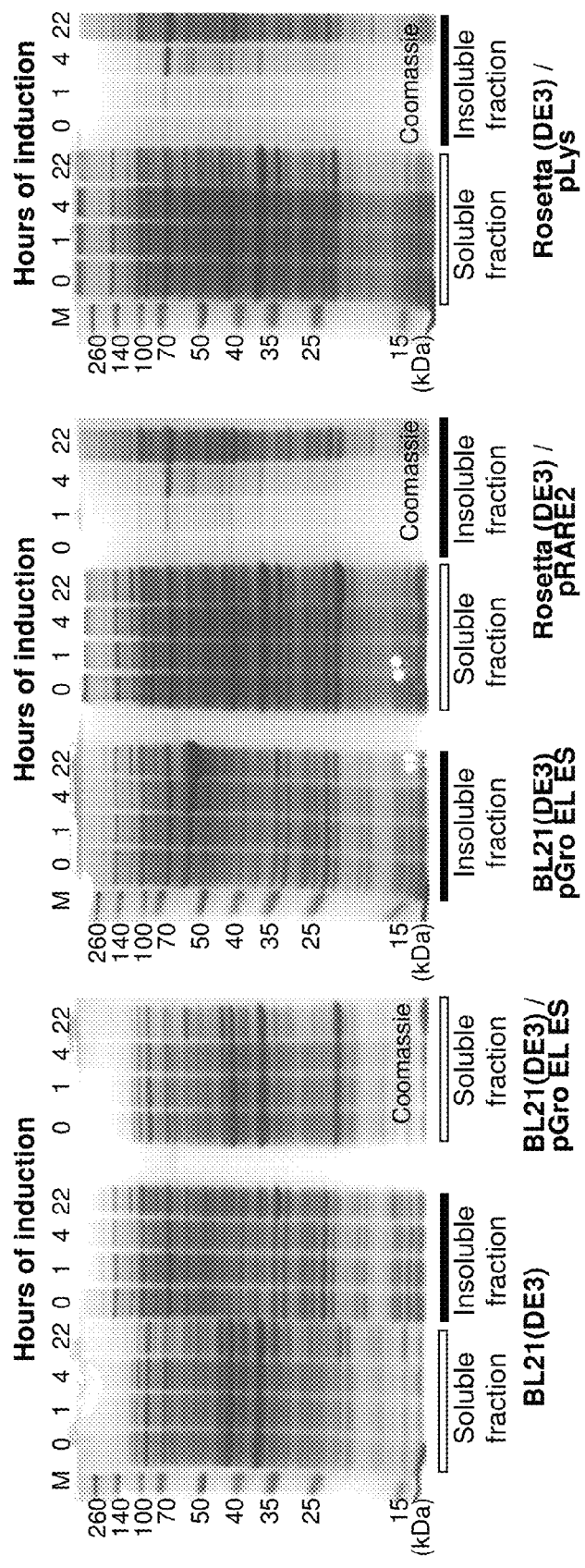
Figure 5:
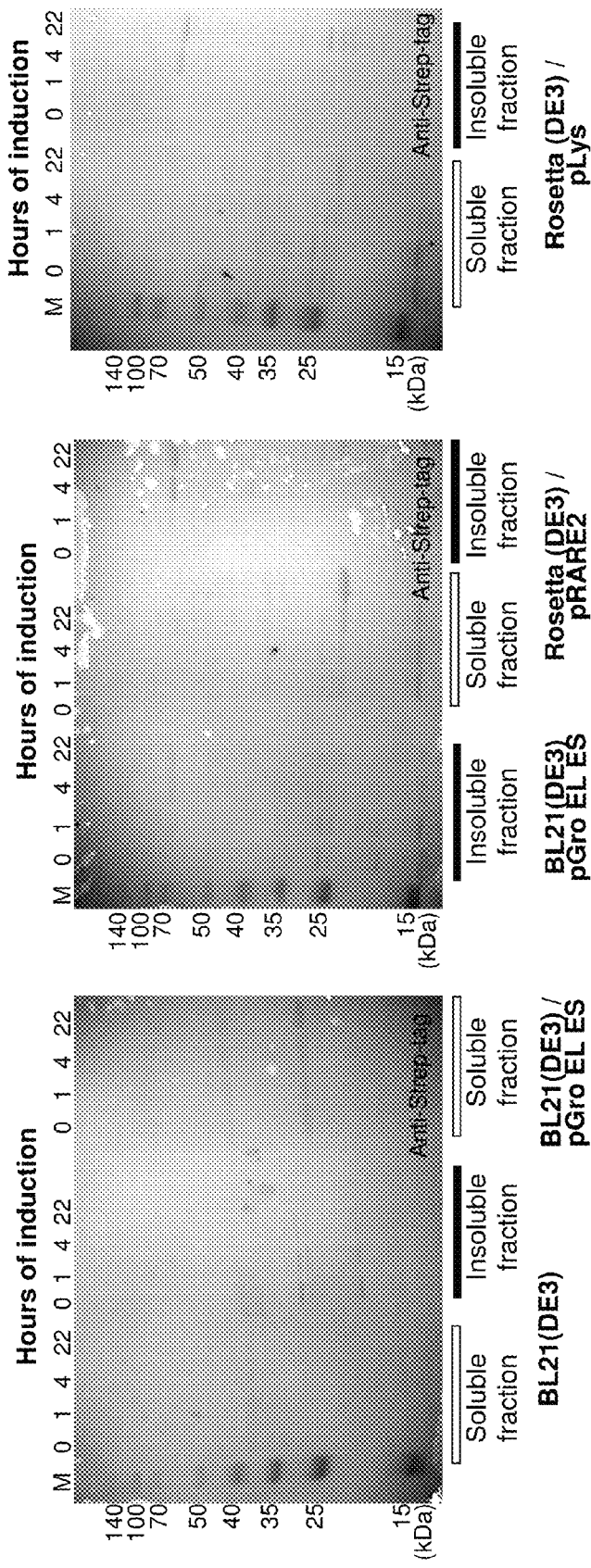
Figure 6:
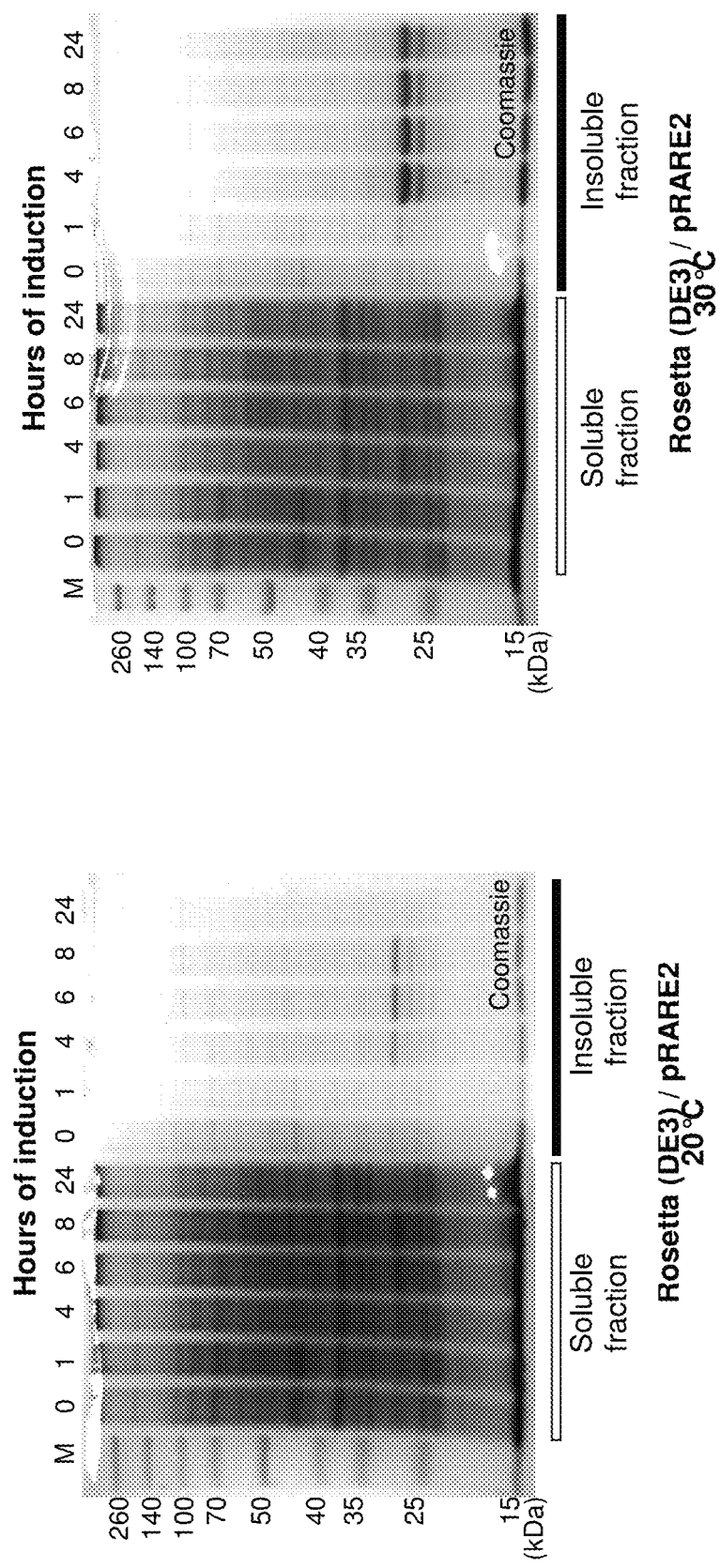
Figure 7:
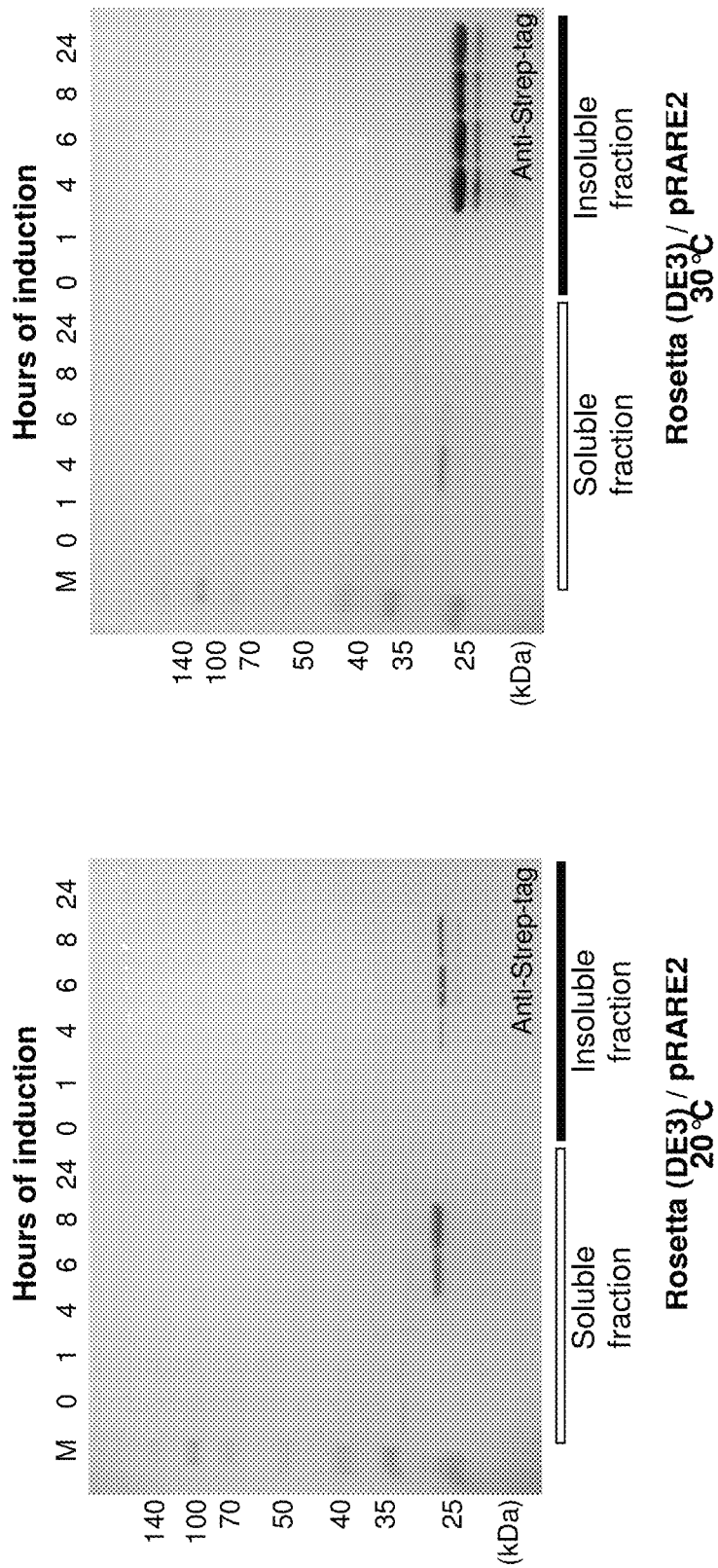
Figure 8:
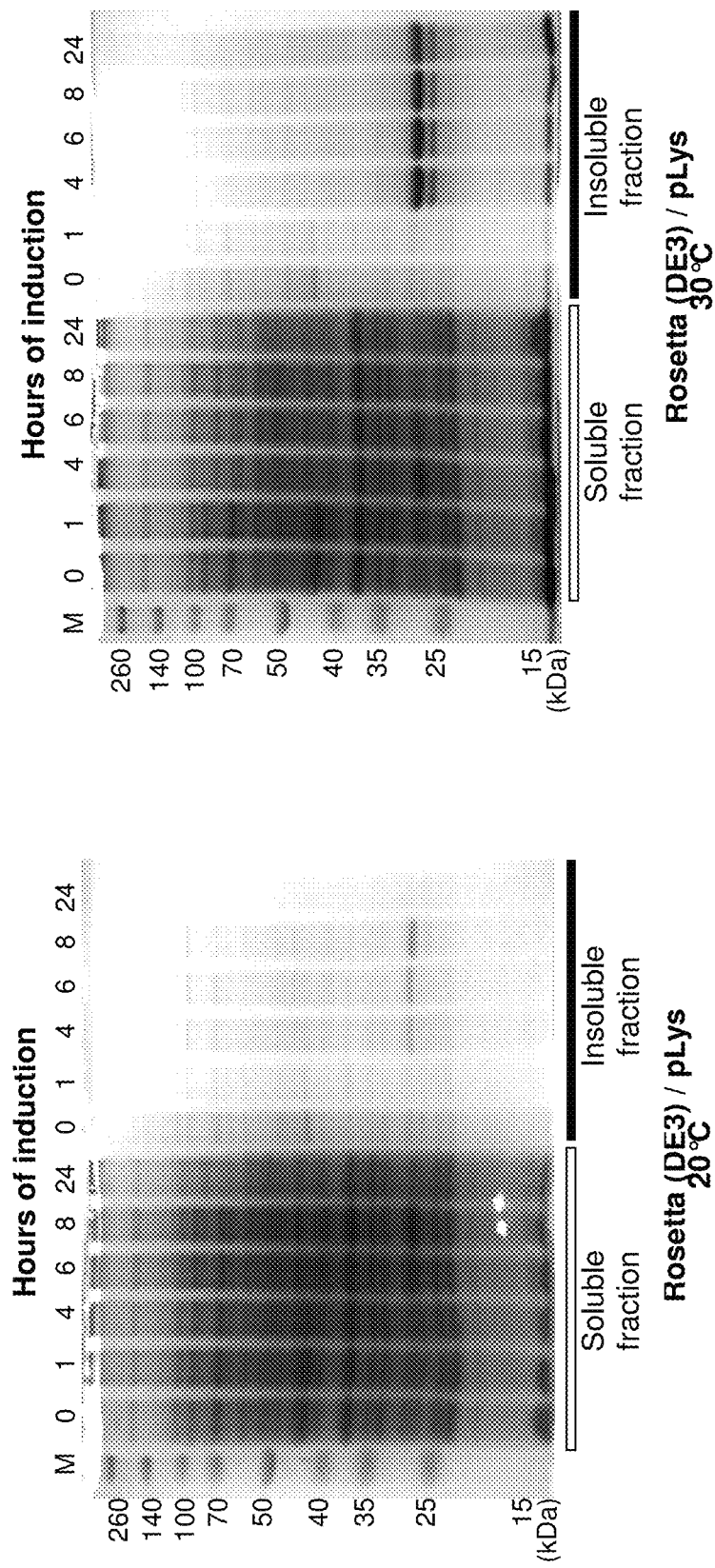
Figure 9:
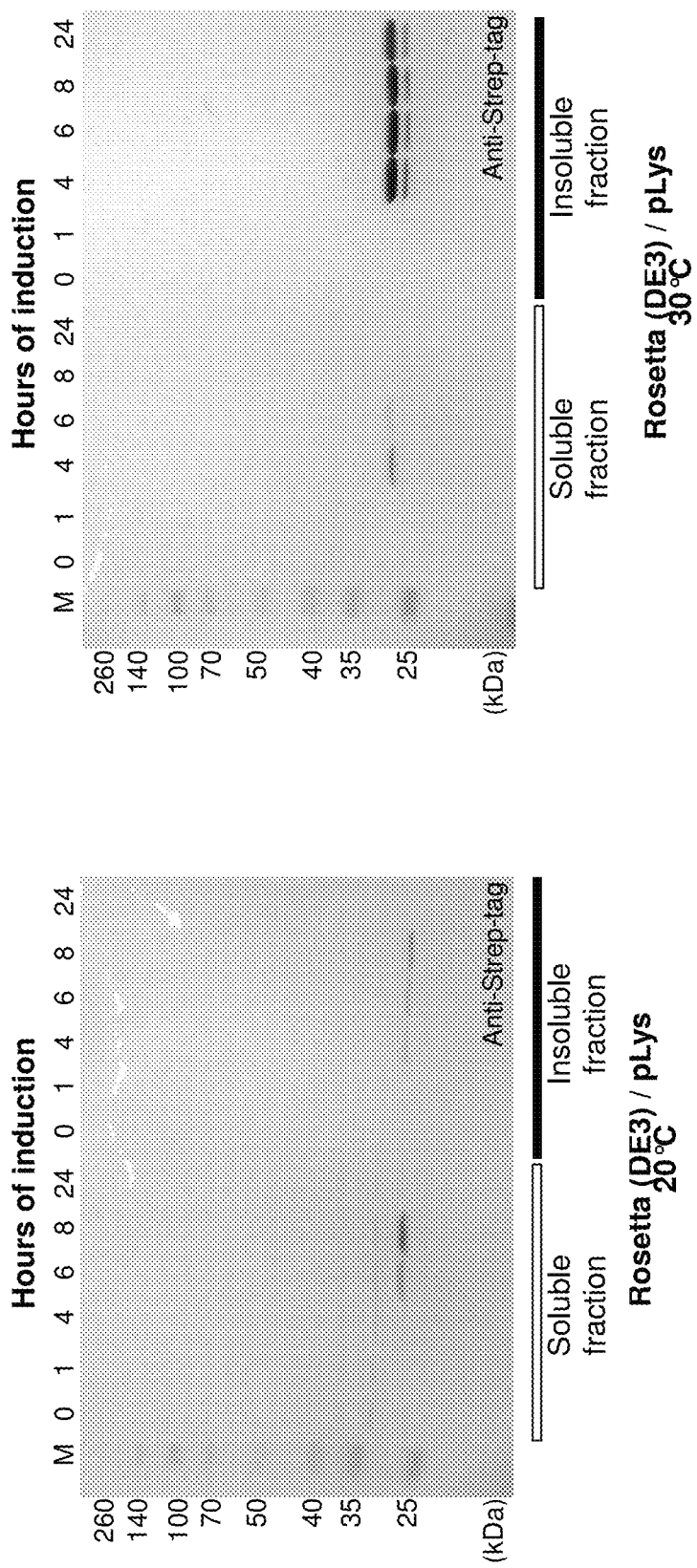

Cells were grown at 37° C. in LB medium supplemented with 200 µg/ml ampicillin (and 30 µg/ml chloramphenicol for the respective strains) until an OD600 of 0.4 was reached. Each culture was shifted to 30° C. and grown until an OD 600 of 0.5 was reached. Cultures were induced with 0.2 mM IPTG and grown for another 22 hours at 30° C. After 0, 1, 4 and 22 hours of induction samples were taken and treated with Bug buster HT solution (Novagen) to break the cells and separate soluble and insoluble protein fractions. Samples were analysed via SDS-PAGE analysis on 12% Gels (and via Western-blot with anti-Strep-tag antibody); see FIGS. 4 and 5. The western-blot analysis revealed the presence of a protein running slightly below the 70 kDa molecular weight marker band in the insoluble protein fraction of the Rosetta(DE3)/pRARE2 and the Rosetta(DE3)/pLys expression after 4-22 hours of induction. A weak protein band detected with the Strep-Tag antibody is also visible in the insoluble protein fraction of the BL21(DE3)/pGroESEL expression after 4-22 hours of induction. Whether this bands correspond to MBP-Casp3.-fusion protein could not be solved.

To optimize the previously tested expression conditions of the pTZE02/Casp 3.1 construct, four further test-expressions were performed. pTZE02/Casp3.1 (KanR) was transformed into the following *E. coli* strains:
Rosetta (DE3)/pRARE2 (CamR)
Rosetta (DE3)/pLys (CamR)

Cells were grown at 37° C. in LB medium supplemented with 50 µg/ml kanamycin and 30 µg/ml chloramphenicol until an OD600 of 0.4 was reached. Each culture was split in two equal parts. One half of each culture was shifted to 30° C., the other half to 20° C. and grown until an OD600 of 0.5 was reached. Cultures were induced with 0.2 mM IPTG and grown for another 24 hours at the respective temperature. After 0, 1, 4, 6, 8 and 24 hours of induction samples were taken and treated with Bug buster HT solution (Novagen) to break the cells and separate soluble and insoluble protein fractions. Samples were analysed via SDS-PAGE analysis on 12% Gels (and via Western-blot with anti-Strep-tag antibody); see FIGS. 6 to 9. Western blot analysis was performed to clearly relate bands in the Coomassie stained gel to the Casp 3.1 target and estimate the amount of soluble compared to insoluble target. To clearly relate bands in the Coomassie stained gel to the Casp 3.1 target and estimate the amount of soluble compared to insoluble target, western blot analysis was performed. The western-blot analysis revealed the presence of a protein running between the 25 and the 35 kDa molecular weight marker band in the soluble and the insoluble protein fraction of all tested expression conditions. The detected protein band in the Rosetta(DE3)/pRARE2 expression at 20° C. (induction for 6-8 hours) is corresponding with the expected molecular weight (30.4 kDa) of the translated Casp3.1 protein and revealed, that at least 50% of the target should be present in a soluble form. Again western-blot analysis revealed the presence of a protein running between the 25 and the 35 kDa molecular weight marker band in the soluble and the insoluble protein fraction of all tested expression conditions. The detected protein band in the Rosetta(DE3)/pLys expression at 20° C. (induction for 6-8 hours) is corresponding with the expected molecular weight (30.4 kDa) of the translated Casp3.1 protein and revealed, that at least 50% of the target should be present in a soluble form. The best expression result was achieved in Rosetta (DE3)/pRARE2 at 20° C. and an induction time of 8 hours.

Example 5

Expression in P. pastoris of pTZP01/Casp3.1 and pHil-D2/Casp3.1

This construct is a pPICZalphaA based vector derivative carrying a secretion signal (α-factor). The final construct is secreted as Procaspase 3.1 with a C-terminal Streptag II. The expected molecular weight of secreted Casp3.1 protein (KEX2 and STE13 coded cleavage site between Arginin and Glutamin at the following recognition site: Glu-Lys-Arg-cleavage site-Glu-Ala-Glu-Ala-Caspase3.1) is 30.4 KDa, with an estimated pI of 8.48. For analyzing the expression pTZP01/Casp3.1 (ZeocinR) was linearized with SalI and transformed into the following P. pastoris strains:
X33
KM71
GS115

Figure 10:
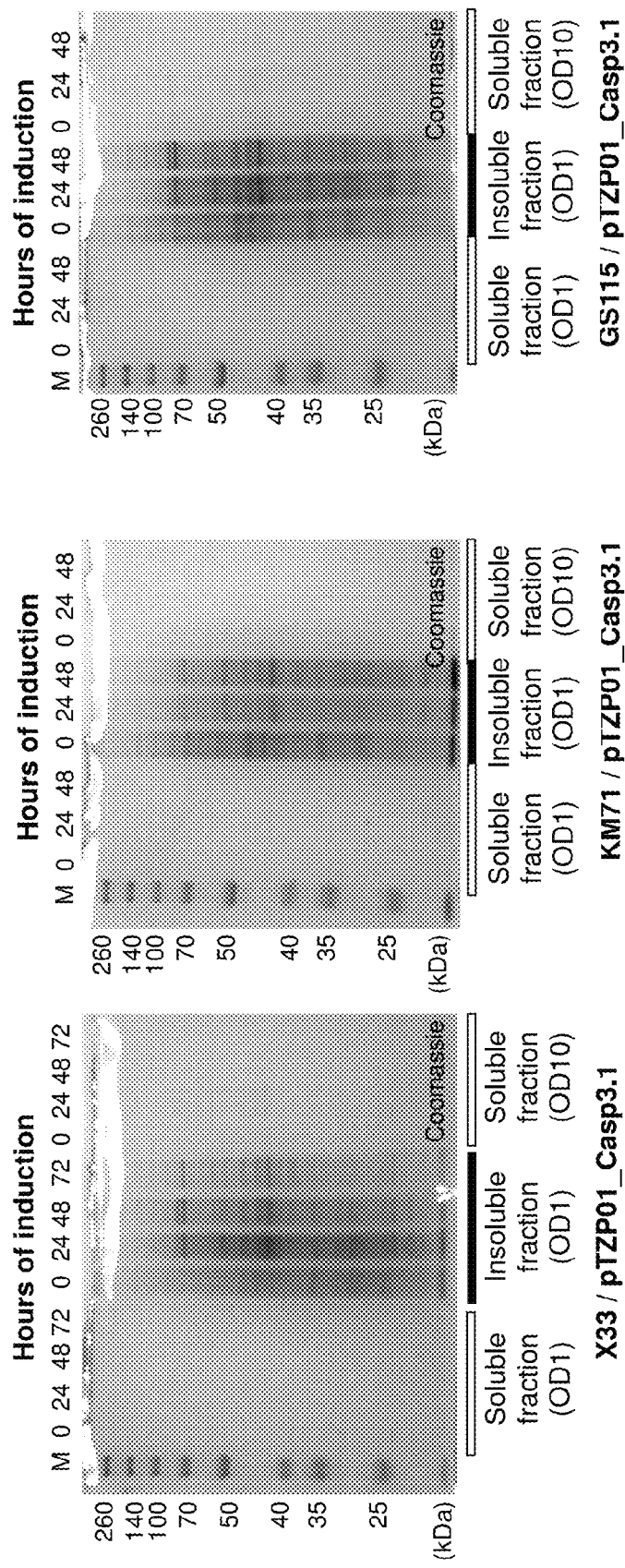
Figure 11:
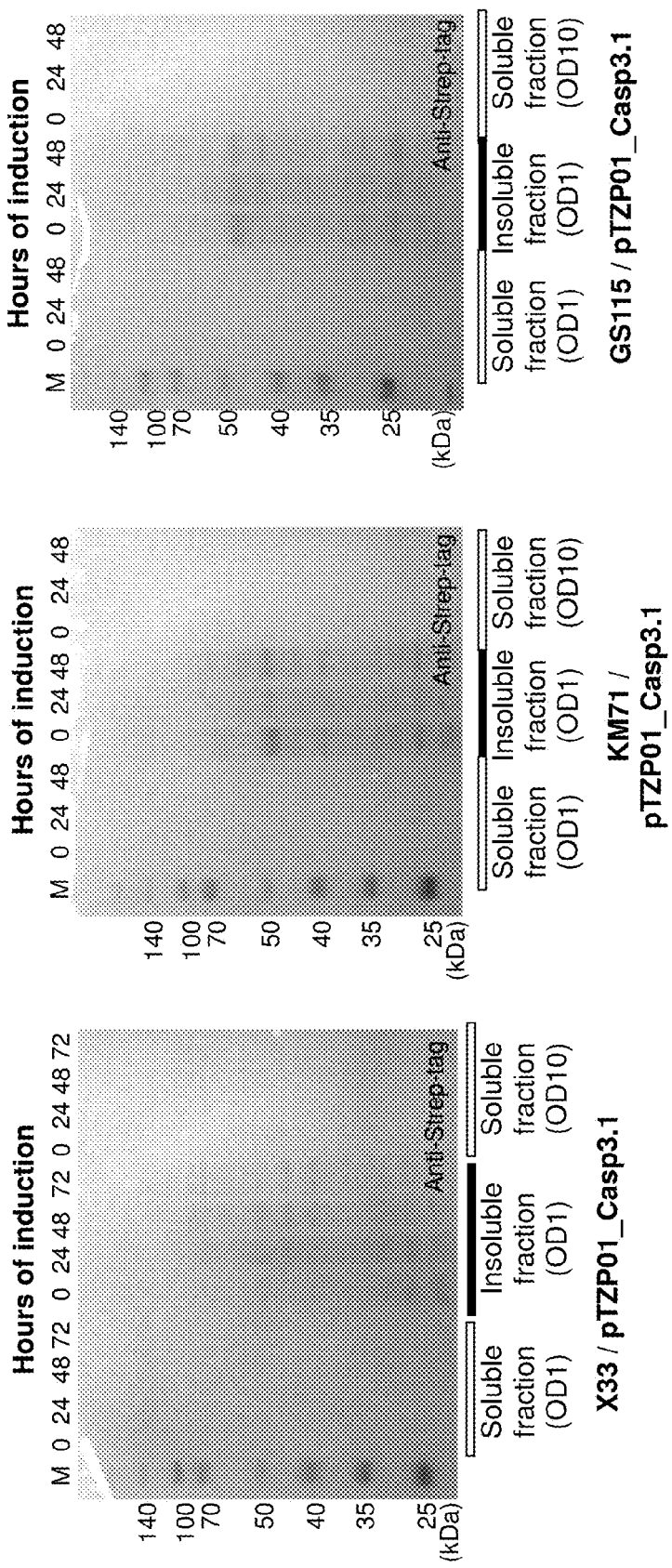

Recombination into the AOX locus was verified by screen-PCR. Recombinant cells were grown at 28° C. in YPD medium for three days (pre-cultures, final OD600 of 16 was reached in the case of KM71 and GS115, OD600 of 18 was reached in the case of X33). Each pre-culture was inoculated in MGY-medium (please refer to the provided Invitrogen manual, supplemented with 0.04% Histidine for KM71 and GS115) and grown until an OD600 of 5 was reached. Cultures were induced with 0.5% (final concentration) methanol and grown for another 72 hours at 28° C. After 0, 24, 48 and 72 hours of induction samples were taken. Glass bead lysis was performed to break the cells and separate soluble and insoluble protein fractions. Samples were analysed via SDS-PAGE analysis on 12% Gels (FIGS. 10 and 11). To clearly identify Casp 3.1 protein bands in the Coomassie stained gel and estimate the amount of soluble compared to insoluble target, western blot analysis with anti-Strep-tag antibody was performed. No protein band running at the expected molecular weight of 30.4 KDa was detectable after the induction with methanol in the western-blot analysis. Nearly no signals were detected in the secreted (soluble) fractions even when ⅙ of an OD600 of 10 was loaded on the gels. Whether this is due to bad or no secretion of the target or due to general bad expression remains unclear.

The final construct pHil-D2/Casp3.1 is expressed intracellularly as Procaspase 3.1 with an N-terminal 6× His-tag. The expected molecular weight of His-Casp3.1 protein is 30 KDa, with an estimated pI of 8.49. For analyzing the expression pHIL-D2/Casp3.1 (AmpR) was linearized with SalI and transformed into the following P. pastoris strains:
KM71
GS115

Figure 12:
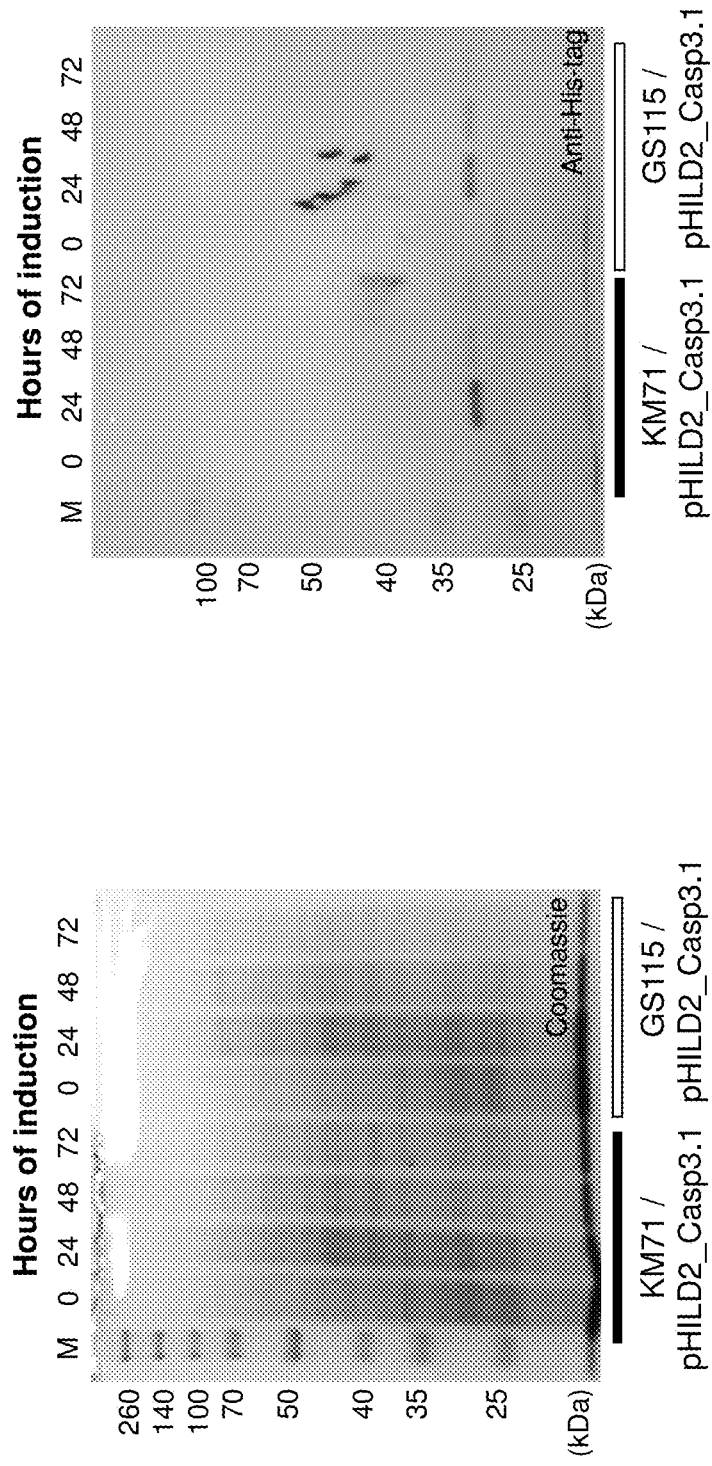

Recombination into the HIS4 locus was verified by screen-PCR. Recombinant cells were grown at 28° C. in SDC medium without histidine for three days (precultures, final OD600 of 4.52 was reached in the case of KM71 and OD600 of 3.29 was reached in the case of GS115). Each pre-culture was inoculated in SDC-medium (without histidine) and grown until an OD600 of 2.5 was reached. Cultures were induced with 0.5% (final concentration) methanol and grown for another 72 hours at 28° C. After 0, 24, 48 and 72 hours of induction samples were taken and treated with glass beads to break the cells. Samples were analysed via SDS-PAGE analysis on 12% Gels (and via Western-blot with anti-Strep-tag antibody); see FIG. 12. A protein band running at the expected molecular weight of 30 KDa was detectable after the induction with methanol in the western-blot analysis. The intensity of the detected protein band seems to decrease the longer the induction lasts. This could either be due to the reduced stability of the produced target over time or due to a decreasing expression over time.

Example 6

Activation of Casp3.1 by BoNT/A

Figure 13:
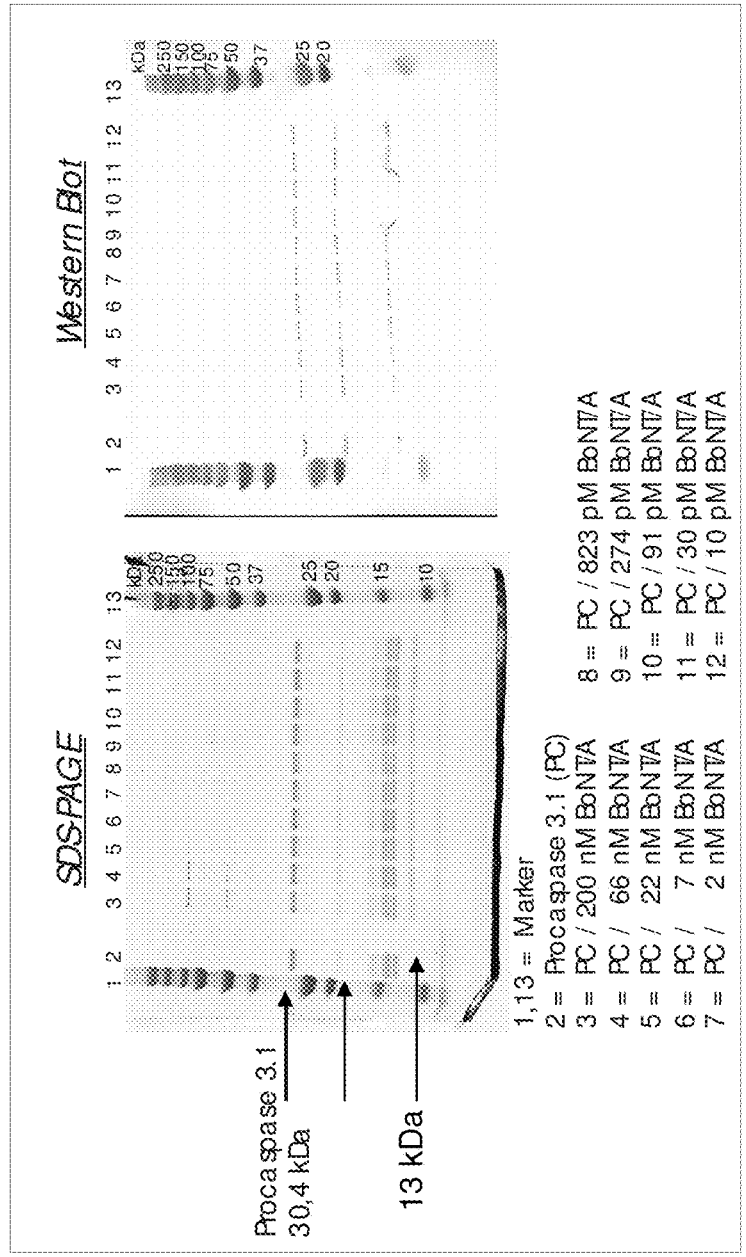

Purified Casp3.1 has been incubated with active BoNT/A for 2 hours at 37° C. The cleavage products obtained by the reaction have been separated by SDS PAGE and further analyzed by Western blotting. The results are shown in FIG. 13. Although there is also some autocatalytic activation of Casp3.1, a dose dependent BoNT/A induced activation of Casp3.1 has also been observed.

The invention claimed is:

1. A polypeptide which exhibits caspase activity comprising a caspase large subunit and a caspase small subunit and a *Clostridium botulinum* or a *Clostridium tetani* neurotoxin cleavage site which upon cleavage activates the caspase activity.

2. The polypeptide of claim 1, wherein the neurotoxin cleavage site is located between the C-terminal proximal region of the caspase large subunit and the N-terminal proximal region of the caspase small subunit.

3. The polypeptide of claim 1, wherein the polypeptide further comprises a prodomain.

4. The polypeptide of claim 3, wherein the neurotoxin cleavage site is located between the C-terminal proximal region of the prodomain and the N-terminal proximal region of the caspase large subunit.

5. The polypeptide of claim 1, wherein the *Clostridium botulinum* neurotoxin cleavage site is a cleavage site recognized and cleaved by a *Clostridium botulinum* neurotoxin type A (BoNT/A) protease.

6. The polypeptide of claim 5, wherein the cleavage site is an amino acid sequence selected from a sequence set forth in SEQ ID NO: 1 to 5.

7. The polypeptide of claim 1, wherein the *Clostridium botulinum* neurotoxin cleavage site is a cleavage site recognized and cleaved by a *Clostridium botulinum* neurotoxin type B (BoNT/B) protease, a *Clostridium botulinum* neurotoxin type C1 (BoNT/C1) protease, a *Clostridium botulinum* neurotoxin type D (BoNT/D) protease, a *Clostridium botulinum* neurotoxin type E (BoNT/E) protease, a *Clostridium botulinum* neurotoxin type F (BoNT/F) protease, a *Clostridium botulinum* neurotoxin type G (BoNT/G) protease, and wherein the *Clostridium tetani* neurotoxin cleavage site is a cleavage site recognized and cleaved by a tetanus neurotoxin (TeNT) protease.

8. A method for determining neurotoxin activity in a sample comprising the steps of:
   (a) contacting the polypeptide of claim 1 with a sample suspected to exhibit neurotoxin activity; and
   (b) measuring caspase activity of the polypeptide, whereby neurotoxin activity in the sample is determined.

9. The method of claim 8, wherein the caspase activity is measured by cleavage of at least one substrate of the polypeptide.

10. The method of claim 9, wherein the substrate is at least one effector caspase.

11. The method of claim 8, wherein the polypeptide is comprised in a host cell.

12. A kit for determining neurotoxin activity comprising the polypeptide of claim 1, and a substrate.

* * * * *

UNITED STATES PATENT AND TRADEMARK OFFICE
CERTIFICATE OF CORRECTION

| | | |
|---|---|---|
| PATENT NO. | : 9,096,886 B2 | Page 1 of 1 |
| APPLICATION NO. | : 14/004259 | |
| DATED | : August 4, 2015 | |
| INVENTOR(S) | : Klaus Fink and Martin Vey | |

It is certified that error appears in the above-identified patent and that said Letters Patent is hereby corrected as shown below:

On the Title Page, item (56) Foreign Patent Documents: "5/2005" should be --8/2005--.

Signed and Sealed this
Fifteenth Day of September, 2015

Michelle K. Lee
*Director of the United States Patent and Trademark Office*

SEQUENCE LISTING

```
<160> NUMBER OF SEQ ID NOS: 16

<210> SEQ ID NO 1
<211> LENGTH: 255
<212> TYPE: PRT
<213> ORGANISM: artificial
<220> FEATURE:
<223> OTHER INFORMATION: caspase mutant

<400> SEQUENCE: 1

Met Asn Ser Tyr Lys Met Asp Tyr Pro Glu Met Gly Leu Cys Ile Ile
1               5                   10                  15

Ile Asn Asn Lys Asn Phe His Lys Ser Thr Gly Met Thr Ser Arg Ser
            20                  25                  30

Gly Thr Asp Val Asp Ala Ala Asn Leu Arg Glu Thr Phe Arg Asn Leu
        35                  40                  45
```

Lys Tyr Glu Val Arg Asn Lys Asn Asp Leu Thr Arg Glu Glu Ile Val
            50                  55                  60

Glu Leu Met Arg Asp Val Ser Lys Glu Asp His Ser Lys Arg Ser Ser
 65                  70                  75                  80

Phe Val Cys Val Leu Leu Ser His Gly Glu Glu Gly Ile Ile Phe Gly
                85                  90                  95

Thr Asn Gly Pro Val Asp Leu Lys Lys Ile Thr Asn Phe Phe Arg Gly
            100                 105                 110

Asp Arg Cys Arg Ser Leu Thr Gly Lys Pro Lys Leu Phe Ile Ile Gln
            115                 120                 125

Ala Cys Arg Gly Thr Glu Leu Asp Cys Gly Ile Glu Gly Gly Gly Thr
130                 135                 140

Arg Ile Asp Glu Ala Asn Gln Arg Ala Thr Lys Met Leu Gly Ser Gly
145                 150                 155                 160

Gly Gly His Lys Ile Pro Val Glu Ala Asp Phe Leu Tyr Ala Tyr Ser
            165                 170                 175

Thr Ala Pro Gly Tyr Tyr Ser Trp Arg Asn Ser Lys Asp Gly Ser Trp
            180                 185                 190

Phe Ile Gln Ser Leu Cys Ala Met Leu Lys Gln Tyr Ala Asp Lys Leu
            195                 200                 205

Glu Phe Met His Ile Leu Thr Arg Val Asn Arg Lys Val Ala Thr Glu
210                 215                 220

Phe Glu Ser Phe Ser Phe Asp Ala Thr Phe His Ala Lys Lys Gln Ile
225                 230                 235                 240

Pro Cys Ile Val Ser Met Leu Thr Lys Glu Leu Tyr Phe Tyr His
            245                 250                 255

<210> SEQ ID NO 2
<211> LENGTH: 252
<212> TYPE: PRT
<213> ORGANISM: artificial
<220> FEATURE:
<223> OTHER INFORMATION: caspase mutant

<400> SEQUENCE: 2

Met Asn Ser Tyr Lys Met Asp Tyr Pro Glu Met Gly Leu Cys Ile Ile
 1               5                  10                  15

Ile Asn Asn Lys Asn Phe His Lys Ser Thr Gly Met Thr Ser Arg Ser
            20                  25                  30

Gly Thr Asp Val Asp Ala Ala Asn Leu Arg Glu Thr Phe Arg Asn Leu
            35                  40                  45

Lys Tyr Glu Val Arg Asn Lys Asn Asp Leu Thr Arg Glu Glu Ile Val
            50                  55                  60

Glu Leu Met Arg Asp Val Ser Lys Glu Asp His Ser Lys Arg Ser Ser
 65                  70                  75                  80

Phe Val Cys Val Leu Leu Ser His Gly Glu Glu Gly Ile Ile Phe Gly
                85                  90                  95

Thr Asn Gly Pro Val Asp Leu Lys Lys Ile Thr Asn Phe Phe Arg Gly
            100                 105                 110

Asp Arg Cys Arg Ser Leu Thr Gly Lys Pro Lys Leu Phe Ile Ile Gln
            115                 120                 125

Ala Cys Arg Gly Thr Glu Leu Asp Cys Gly Ile Glu Gly Gly Gly Gly
130                 135                 140

Ile Asp Glu Ala Asn Gln Arg Ala Thr Lys Met Gly Gly Gly Gly His
145                 150                 155                 160

```
Lys Ile Pro Val Glu Ala Asp Phe Leu Tyr Ala Tyr Ser Thr Ala Pro
                165                 170                 175

Gly Tyr Tyr Ser Trp Arg Asn Ser Lys Asp Gly Ser Trp Phe Ile Gln
            180                 185                 190

Ser Leu Cys Ala Met Leu Lys Gln Tyr Ala Asp Lys Leu Glu Phe Met
        195                 200                 205

His Ile Leu Thr Arg Val Asn Arg Lys Val Ala Thr Glu Phe Glu Ser
    210                 215                 220

Phe Ser Phe Asp Ala Thr Phe His Ala Lys Lys Gln Ile Pro Cys Ile
225                 230                 235                 240

Val Ser Met Leu Thr Lys Glu Leu Tyr Phe Tyr His
                245                 250
```

<210> SEQ ID NO 3
<211> LENGTH: 171
<212> TYPE: PRT
<213> ORGANISM: artificial
<220> FEATURE:
<223> OTHER INFORMATION: caspase mutant

<400> SEQUENCE: 3

```
Met Asn Ser Tyr Lys Met Asp Tyr Pro Glu Met Gly Leu Cys Ile Ile
1               5                   10                  15

Ile Asn Asn Lys Asn Phe His Lys Ser Thr Gly Met Thr Ser Arg Ser
            20                  25                  30

Gly Thr Asp Val Asp Ala Ala Asn Leu Arg Glu Thr Phe Arg Asn Leu
        35                  40                  45

Lys Tyr Glu Val Arg Asn Lys Asn Asp Leu Thr Arg Glu Glu Ile Val
    50                  55                  60

Glu Leu Met Arg Asp Val Ser Lys Glu Asp His Ser Lys Arg Ser Ser
65                  70                  75                  80

Phe Val Cys Val Leu Leu Ser His Gly Glu Glu Gly Ile Ile Phe Gly
                85                  90                  95

Thr Asn Gly Pro Val Asp Leu Lys Lys Ile Thr Asn Phe Phe Arg Gly
            100                 105                 110

Asp Arg Cys Arg Ser Leu Thr Gly Lys Pro Lys Leu Phe Ile Ile Gln
        115                 120                 125

Ala Cys Arg Gly Thr Glu Leu Asp Cys Gly Ile Glu Ile Asp Glu Ala
    130                 135                 140

Asn Gln Arg Ala Thr Lys Met His Lys Ile Pro Val Glu Ala Asp Phe
145                 150                 155                 160

Leu Tyr Ala Tyr Ser Thr Ala Pro Gly Tyr His
                165                 170
```

<210> SEQ ID NO 4
<211> LENGTH: 292
<212> TYPE: PRT
<213> ORGANISM: artificial
<220> FEATURE:
<223> OTHER INFORMATION: caspase mutant

<400> SEQUENCE: 4

```
Met Glu Asn Thr Glu Asn Ser Val Asp Ser Lys Ser Ile Lys Asn Leu
1               5                   10                  15

Glu Pro Lys Ile Ile His Gly Ser Glu Ser Met Asp Ser Gly Ile Ser
            20                  25                  30

Leu Asp Asn Ser Tyr Lys Met Asp Tyr Pro Glu Met Gly Leu Cys Ile
        35                  40                  45
```

```
Ile Ile Asn Asn Lys Asn Phe His Lys Ser Thr Gly Met Thr Ser Arg
 50                  55                  60

Ser Gly Thr Asp Val Asp Ala Ala Asn Leu Arg Glu Thr Phe Arg Asn
 65                  70                  75                  80

Leu Lys Tyr Glu Val Arg Asn Lys Asn Asp Leu Thr Arg Glu Glu Ile
                 85                  90                  95

Val Glu Leu Met Arg Asp Val Ser Lys Glu Asp His Ser Lys Arg Ser
             100                 105                 110

Ser Phe Val Cys Val Leu Leu Ser His Gly Glu Glu Gly Ile Ile Phe
             115                 120                 125

Gly Thr Asn Gly Pro Val Asp Leu Lys Lys Ile Thr Asn Phe Phe Arg
             130                 135                 140

Gly Asp Arg Cys Arg Ser Leu Thr Gly Lys Pro Lys Leu Phe Ile Ile
145                 150                 155                 160

Gln Ala Cys Arg Gly Thr Glu Leu Asp Cys Gly Ile Glu Thr Asp Ser
                165                 170                 175

Gly Ile Asp Glu Ala Asn Gln Arg Ala Thr Lys Met Leu Gly Ser Gly
            180                 185                 190

Val Asp Asp Asp Met Ala Cys His Lys Ile Pro Val Glu Ala Asp Phe
            195                 200                 205

Leu Tyr Ala Tyr Ser Thr Ala Pro Gly Tyr Tyr Ser Trp Arg Asn Ser
    210                 215                 220

Lys Asp Gly Ser Trp Phe Ile Gln Ser Leu Cys Ala Met Leu Lys Gln
225                 230                 235                 240

Tyr Ala Asp Lys Leu Glu Phe Met His Ile Leu Thr Arg Val Asn Arg
                245                 250                 255

Lys Val Thr Glu Phe Glu Ser Phe Ser Phe Asp Ala Thr Phe His
            260                 265                 270

Ala Lys Lys Gln Ile Pro Cys Ile Val Ser Met Leu Thr Lys Glu Leu
            275                 280                 285

Tyr Phe Tyr His
    290

<210> SEQ ID NO 5
<211> LENGTH: 288
<212> TYPE: PRT
<213> ORGANISM: artificial
<220> FEATURE:
<223> OTHER INFORMATION: caspase mutant

<400> SEQUENCE: 5

Met Glu Asn Thr Glu Asn Ser Val Asp Ser Lys Ser Ile Lys Asn Leu
1               5                  10                  15

Glu Pro Lys Ile Ile His Gly Ser Glu Ser Met Asp Ser Gly Ile Ser
                20                  25                  30

Leu Asp Asn Ser Tyr Lys Met Asp Tyr Pro Glu Met Gly Leu Cys Ile
            35                  40                  45

Ile Ile Asn Asn Lys Asn Phe His Lys Ser Thr Gly Met Thr Ser Arg
 50                  55                  60

Ser Gly Thr Asp Val Asp Ala Ala Asn Leu Arg Glu Thr Phe Arg Asn
 65                  70                  75                  80

Leu Lys Tyr Glu Val Arg Asn Lys Asn Asp Leu Thr Arg Glu Glu Ile
                 85                  90                  95

Val Glu Leu Met Arg Asp Val Ser Lys Glu Asp His Ser Lys Arg Ser
             100                 105                 110
```

```
Ser Phe Val Cys Val Leu Leu Ser His Gly Glu Gly Ile Ile Phe
            115                 120                 125

Gly Thr Asn Gly Pro Val Asp Leu Lys Lys Ile Thr Asn Phe Phe Arg
        130                 135                 140

Gly Asp Arg Cys Arg Ser Leu Thr Gly Lys Pro Lys Leu Phe Ile Ile
145                 150                 155                 160

Gln Ala Cys Arg Gly Thr Glu Leu Asp Cys Gly Ile Glu Thr Asp Ser
                165                 170                 175

Gly Ile Asp Glu Ala Asn Gln Arg Ala Thr Lys Met Val Asp Asp
            180                 185                 190

Met Ala Cys His Lys Ile Pro Val Glu Ala Asp Phe Leu Tyr Ala Tyr
        195                 200                 205

Ser Thr Ala Pro Gly Tyr Tyr Ser Trp Arg Asn Ser Lys Asp Gly Ser
            210                 215                 220

Trp Phe Ile Gln Ser Leu Cys Ala Met Leu Lys Gln Tyr Ala Asp Lys
225                 230                 235                 240

Leu Glu Phe Met His Ile Leu Thr Arg Val Asn Arg Lys Val Ala Thr
                245                 250                 255

Glu Phe Glu Ser Phe Ser Phe Asp Ala Thr Phe His Ala Lys Lys Gln
            260                 265                 270

Ile Pro Cys Ile Val Ser Met Leu Thr Lys Glu Leu Tyr Phe Tyr His
        275                 280                 285

<210> SEQ ID NO 6
<211> LENGTH: 416
<212> TYPE: PRT
<213> ORGANISM: Homo sapiens

<400> SEQUENCE: 6

Met Asp Glu Ala Asp Arg Arg Leu Leu Arg Arg Cys Arg Leu Arg Leu
1               5                   10                  15

Val Glu Glu Leu Gln Val Asp Gln Leu Trp Asp Ala Leu Leu Ser Arg
            20                  25                  30

Glu Leu Phe Arg Pro His Met Ile Glu Asp Ile Gln Arg Ala Gly Ser
        35                  40                  45

Gly Ser Arg Arg Asp Gln Ala Arg Gln Leu Ile Ile Asp Leu Glu Thr
    50                  55                  60

Arg Gly Ser Gln Ala Leu Pro Leu Phe Ile Ser Cys Leu Glu Asp Thr
65                  70                  75                  80

Gly Gln Asp Met Leu Ala Ser Phe Leu Arg Thr Asn Arg Gln Ala Ala
                85                  90                  95

Lys Leu Ser Lys Pro Thr Leu Glu Asn Leu Thr Pro Val Val Leu Arg
            100                 105                 110

Pro Glu Ile Arg Lys Pro Glu Val Leu Arg Pro Glu Thr Pro Arg Pro
        115                 120                 125

Val Asp Ile Gly Ser Gly Gly Phe Gly Asp Val Gly Ala Leu Glu Ser
    130                 135                 140

Leu Arg Gly Asn Ala Asp Leu Ala Tyr Ile Leu Ser Met Glu Pro Cys
145                 150                 155                 160

Gly His Cys Leu Ile Ile Asn Asn Val Asn Phe Cys Arg Glu Ser Gly
                165                 170                 175

Leu Arg Thr Arg Thr Gly Ser Asn Ile Asp Cys Glu Lys Leu Arg Arg
            180                 185                 190

Arg Phe Ser Ser Leu His Phe Met Val Glu Val Lys Gly Asp Leu Thr
```

```
            195                 200                 205
Ala Lys Lys Met Val Leu Ala Leu Leu Glu Leu Ala Gln Gln Asp His
    210                 215                 220

Gly Ala Leu Asp Cys Cys Val Val Ile Leu Ser His Gly Cys Gln
225                 230                 235                 240

Ala Ser His Leu Gln Phe Pro Gly Ala Val Tyr Gly Thr Asp Gly Cys
                245                 250                 255

Pro Val Ser Val Glu Lys Ile Val Asn Ile Phe Asn Gly Thr Ser Cys
                260                 265                 270

Pro Ser Leu Gly Gly Lys Pro Lys Leu Phe Phe Ile Gln Ala Cys Gly
                275                 280                 285

Gly Glu Gln Lys Asp His Gly Phe Glu Val Ala Ser Thr Ser Pro Glu
    290                 295                 300

Asp Glu Ser Pro Gly Ser Asn Pro Glu Pro Asp Ala Thr Pro Phe Gln
305                 310                 315                 320

Glu Gly Leu Arg Thr Phe Asp Gln Leu Asp Ala Ile Ser Ser Leu Pro
                325                 330                 335

Thr Pro Ser Asp Ile Phe Val Ser Tyr Ser Thr Phe Pro Gly Phe Val
                340                 345                 350

Ser Trp Arg Asp Pro Lys Ser Gly Ser Trp Tyr Val Glu Thr Leu Asp
                355                 360                 365

Asp Ile Phe Glu Gln Trp Ala His Ser Glu Asp Leu Gln Ser Leu Leu
    370                 375                 380

Leu Arg Val Ala Asn Ala Val Ser Val Lys Gly Ile Tyr Lys Gln Met
385                 390                 395                 400

Pro Gly Cys Phe Asn Phe Leu Arg Lys Lys Leu Phe Phe Lys Thr Ser
                405                 410                 415

<210> SEQ ID NO 7
<211> LENGTH: 277
<212> TYPE: PRT
<213> ORGANISM: Homo sapiens

<400> SEQUENCE: 7

Met Glu Asn Thr Glu Asn Ser Val Asp Ser Lys Ser Ile Lys Asn Leu
1               5                   10                  15

Glu Pro Lys Ile Ile His Gly Ser Glu Ser Met Asp Ser Gly Ile Ser
                20                  25                  30

Leu Asp Asn Ser Tyr Lys Met Asp Tyr Pro Glu Met Gly Leu Cys Ile
            35                  40                  45

Ile Ile Asn Asn Lys Asn Phe His Lys Ser Thr Gly Met Thr Ser Arg
        50                  55                  60

Ser Gly Thr Asp Val Asp Ala Ala Asn Leu Arg Glu Thr Phe Arg Asn
65                  70                  75                  80

Leu Lys Tyr Glu Val Arg Asn Lys Asn Asp Leu Thr Arg Glu Glu Ile
                85                  90                  95

Val Glu Leu Met Arg Asp Val Ser Lys Glu Asp His Ser Lys Arg Ser
                100                 105                 110

Ser Phe Val Cys Val Leu Leu Ser His Gly Glu Glu Gly Ile Ile Phe
            115                 120                 125

Gly Thr Asn Gly Pro Val Asp Leu Lys Lys Ile Thr Asn Phe Phe Arg
        130                 135                 140

Gly Asp Arg Cys Arg Ser Leu Thr Gly Lys Pro Lys Leu Phe Ile Ile
145                 150                 155                 160
```

```
Gln Ala Cys Arg Gly Thr Glu Leu Asp Cys Gly Ile Glu Thr Asp Ser
                165                 170                 175

Gly Val Asp Asp Met Ala Cys His Lys Ile Pro Val Glu Ala Asp
            180                 185                 190

Phe Leu Tyr Ala Tyr Ser Thr Ala Pro Gly Tyr Tyr Ser Trp Arg Asn
            195                 200                 205

Ser Lys Asp Gly Ser Trp Phe Ile Gln Ser Leu Cys Ala Met Leu Lys
        210                 215                 220

Gln Tyr Ala Asp Lys Leu Glu Phe Met His Ile Leu Thr Arg Val Asn
225                 230                 235                 240

Arg Lys Val Ala Thr Glu Phe Glu Ser Phe Ser Phe Asp Ala Thr Phe
                245                 250                 255

His Ala Lys Lys Gln Ile Pro Cys Ile Val Ser Met Leu Thr Lys Glu
            260                 265                 270

Leu Tyr Phe Tyr His
            275

<210> SEQ ID NO 8
<211> LENGTH: 479
<212> TYPE: PRT
<213> ORGANISM: Homo sapiens

<400> SEQUENCE: 8

Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

Gln Glu Lys Arg Met Leu Glu Glu Ser Asn Leu Ser Phe Leu Lys Glu
    50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
        115                 120                 125

Ser Lys Cys Lys Leu Asp Asp Asp Met Asn Leu Leu Asp Ile Phe Ile
    130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Glu Arg Ser Ser Ser Leu Glu Gly Ser
            180                 185                 190

Pro Asp Glu Phe Ser Asn Gly Glu Glu Leu Cys Gly Val Met Thr Ile
        195                 200                 205

Ser Asp Ser Pro Arg Glu Gln Asp Ser Glu Ser Gln Thr Leu Asp Lys
    210                 215                 220

Val Tyr Gln Met Lys Ser Lys Pro Arg Gly Tyr Cys Leu Ile Ile Asn
225                 230                 235                 240

Asn His Asn Phe Ala Lys Ala Arg Glu Lys Val Pro Lys Leu His Ser
                245                 250                 255
```

```
Ile Arg Asp Arg Asn Gly Thr His Leu Asp Ala Gly Ala Leu Thr Thr
            260                 265                 270

Thr Phe Glu Glu Leu His Phe Glu Ile Lys Pro His Asp Asp Cys Thr
        275                 280                 285

Val Glu Gln Ile Tyr Glu Ile Leu Lys Ile Tyr Gln Leu Met Asp His
    290                 295                 300

Ser Asn Met Asp Cys Phe Ile Cys Cys Ile Leu Ser His Gly Asp Lys
305                 310                 315                 320

Gly Ile Ile Tyr Gly Thr Asp Gly Gln Glu Ala Pro Ile Tyr Glu Leu
                325                 330                 335

Thr Ser Gln Phe Thr Gly Leu Lys Cys Pro Ser Leu Ala Gly Lys Pro
        340                 345                 350

Lys Val Phe Phe Ile Gln Ala Cys Gln Gly Asp Asn Tyr Gln Lys Gly
            355                 360                 365

Ile Pro Val Glu Thr Asp Ser Glu Glu Gln Pro Tyr Leu Glu Met Asp
        370                 375                 380

Leu Ser Ser Pro Gln Thr Arg Tyr Ile Pro Asp Glu Ala Asp Phe Leu
385                 390                 395                 400

Leu Gly Met Ala Thr Val Asn Asn Cys Val Ser Tyr Arg Asn Pro Ala
                405                 410                 415

Glu Gly Thr Trp Tyr Ile Gln Ser Leu Cys Gln Ser Leu Arg Glu Arg
            420                 425                 430

Cys Pro Arg Gly Asp Asp Ile Leu Thr Ile Leu Thr Glu Val Asn Tyr
        435                 440                 445

Glu Val Ser Asn Lys Asp Asp Lys Lys Asn Met Gly Lys Gln Met Pro
    450                 455                 460

Gln Pro Thr Phe Thr Leu Arg Lys Lys Leu Val Phe Pro Ser Asp
465                 470                 475

<210> SEQ ID NO 9
<211> LENGTH: 521
<212> TYPE: PRT
<213> ORGANISM: Homo sapiens

<400> SEQUENCE: 9

Met Lys Ser Gln Gly Gln His Trp Tyr Ser Ser Asp Lys Asn Cys
1               5                   10                  15

Lys Val Ser Phe Arg Glu Lys Leu Leu Ile Ile Asp Ser Asn Leu Gly
                20                  25                  30

Val Gln Asp Val Glu Asn Leu Lys Phe Leu Cys Ile Gly Leu Val Pro
        35                  40                  45

Asn Lys Lys Leu Glu Lys Ser Ser Ala Ser Asp Val Phe Glu His
50                  55                  60

Leu Leu Ala Glu Asp Leu Leu Ser Glu Glu Asp Pro Phe Phe Leu Ala
65                  70                  75                  80

Glu Leu Leu Tyr Ile Ile Arg Gln Lys Lys Leu Leu Gln His Leu Asn
                85                  90                  95

Cys Thr Lys Glu Glu Val Glu Arg Leu Leu Pro Thr Arg Gln Arg Val
            100                 105                 110

Ser Leu Phe Arg Asn Leu Leu Tyr Glu Leu Ser Glu Gly Ile Asp Ser
        115                 120                 125

Glu Asn Leu Lys Asp Met Ile Phe Leu Leu Lys Asp Ser Leu Pro Lys
    130                 135                 140

Thr Glu Met Thr Ser Leu Ser Phe Leu Ala Phe Leu Glu Lys Gln Gly
```

```
                145                 150                 155                 160
Lys Ile Asp Glu Asp Asn Leu Thr Cys Leu Glu Asp Leu Cys Lys Thr
                165                 170                 175

Val Val Pro Lys Leu Leu Arg Asn Ile Glu Lys Tyr Lys Arg Glu Lys
            180                 185                 190

Ala Ile Gln Ile Val Thr Pro Pro Val Asp Lys Glu Ala Glu Ser Tyr
            195                 200                 205

Gln Gly Glu Glu Glu Leu Val Ser Gln Thr Asp Val Lys Thr Phe Leu
        210                 215                 220

Glu Ala Leu Pro Gln Glu Ser Trp Gln Asn Lys His Ala Gly Ser Asn
225                 230                 235                 240

Gly Asn Arg Ala Thr Asn Gly Ala Pro Ser Leu Val Ser Arg Gly Met
                245                 250                 255

Gln Gly Ala Ser Ala Asn Thr Leu Asn Ser Glu Thr Ser Thr Lys Arg
            260                 265                 270

Ala Ala Val Tyr Arg Met Asn Arg Asn His Arg Gly Leu Cys Val Ile
            275                 280                 285

Val Asn Asn His Ser Phe Thr Ser Leu Lys Asp Arg Gln Gly Thr His
        290                 295                 300

Lys Asp Ala Glu Ile Leu Ser His Val Phe Gln Trp Leu Gly Phe Thr
305                 310                 315                 320

Val His Ile His Asn Asn Val Thr Lys Val Glu Met Glu Met Val Leu
                325                 330                 335

Gln Lys Gln Lys Cys Asn Pro Ala His Ala Asp Gly Asp Cys Phe Val
            340                 345                 350

Phe Cys Ile Leu Thr His Gly Arg Phe Gly Ala Val Tyr Ser Ser Asp
            355                 360                 365

Glu Ala Leu Ile Pro Ile Arg Glu Ile Met Ser His Phe Thr Ala Leu
        370                 375                 380

Gln Cys Pro Arg Leu Ala Glu Lys Pro Lys Leu Phe Phe Ile Gln Ala
385                 390                 395                 400

Cys Gln Gly Glu Glu Ile Gln Pro Ser Val Ser Ile Glu Ala Asp Ala
                405                 410                 415

Leu Asn Pro Glu Gln Ala Pro Thr Ser Leu Gln Asp Ser Ile Pro Ala
            420                 425                 430

Glu Ala Asp Phe Leu Leu Gly Leu Ala Thr Val Pro Gly Tyr Val Ser
            435                 440                 445

Phe Arg His Val Glu Glu Gly Ser Trp Tyr Ile Gln Ser Leu Cys Asn
450                 455                 460

His Leu Lys Lys Leu Val Pro Arg Met Leu Lys Phe Leu Glu Lys Thr
465                 470                 475                 480

Met Glu Ile Arg Gly Arg Lys Arg Thr Val Trp Gly Ala Lys Gln Ile
                485                 490                 495

Ser Ala Thr Ser Leu Pro Thr Ala Ile Ser Ala Gln Thr Pro Arg Pro
            500                 505                 510

Pro Met Arg Arg Trp Ser Ser Val Ser
            515                 520

<210> SEQ ID NO 10
<211> LENGTH: 452
<212> TYPE: PRT
<213> ORGANISM: Homo sapiens

<400> SEQUENCE: 10
```

```
Met Ala Ala Pro Ser Ala Gly Ser Trp Ser Thr Phe Gln His Lys Glu
1               5                   10                  15

Leu Met Ala Ala Asp Arg Gly Arg Ile Leu Gly Val Cys Gly Met
            20                  25                  30

His Pro His His Gln Glu Thr Leu Lys Lys Asn Arg Val Val Leu Ala
        35                  40                  45

Lys Gln Leu Leu Leu Ser Glu Leu Leu Glu His Leu Leu Glu Lys Asp
    50                  55                  60

Ile Ile Thr Leu Glu Met Arg Glu Leu Ile Gln Ala Lys Val Gly Ser
65                  70                  75                  80

Phe Ser Gln Asn Val Glu Leu Leu Asn Leu Leu Pro Lys Arg Gly Pro
                85                  90                  95

Gln Ala Phe Asp Ala Phe Cys Glu Ala Leu Arg Glu Thr Lys Gln Gly
            100                 105                 110

His Leu Glu Asp Met Leu Leu Thr Thr Leu Ser Gly Leu Gln His Val
        115                 120                 125

Leu Pro Pro Leu Ser Cys Asp Tyr Asp Leu Ser Leu Pro Phe Pro Val
    130                 135                 140

Cys Glu Ser Cys Pro Leu Tyr Lys Lys Leu Arg Leu Ser Thr Asp Thr
145                 150                 155                 160

Val Glu His Ser Leu Asp Asn Lys Asp Gly Pro Val Cys Leu Gln Val
                165                 170                 175

Lys Pro Cys Thr Pro Glu Phe Tyr Gln Thr His Phe Gln Leu Ala Tyr
            180                 185                 190

Arg Leu Gln Ser Arg Pro Arg Gly Leu Ala Leu Val Leu Ser Asn Val
        195                 200                 205

His Phe Thr Gly Glu Lys Glu Leu Glu Phe Arg Ser Gly Gly Asp Val
    210                 215                 220

Asp His Ser Thr Leu Val Thr Leu Phe Lys Leu Leu Gly Tyr Asp Val
225                 230                 235                 240

His Val Leu Cys Asp Gln Thr Ala Gln Glu Met Gln Glu Lys Leu Gln
                245                 250                 255

Asn Phe Ala Gln Leu Pro Ala His Arg Val Thr Asp Ser Cys Ile Val
            260                 265                 270

Ala Leu Leu Ser His Gly Val Glu Gly Ala Ile Tyr Gly Val Asp Gly
        275                 280                 285

Lys Leu Leu Gln Leu Gln Glu Val Phe Gln Leu Phe Asp Asn Ala Asn
    290                 295                 300

Cys Pro Ser Leu Gln Asn Lys Pro Lys Met Phe Phe Ile Gln Ala Cys
305                 310                 315                 320

Arg Gly Asp Glu Thr Asp Arg Gly Val Asp Gln Gln Asp Gly Lys Asn
                325                 330                 335

His Ala Gly Ser Pro Gly Cys Glu Glu Ser Asp Ala Gly Lys Glu Lys
            340                 345                 350

Leu Pro Lys Met Arg Leu Pro Thr Arg Ser Asp Met Ile Cys Gly Tyr
        355                 360                 365

Ala Cys Leu Lys Gly Thr Ala Ala Met Arg Asn Thr Lys Arg Gly Ser
    370                 375                 380

Trp Tyr Ile Glu Ala Leu Ala Gln Val Phe Ser Glu Arg Ala Cys Asp
385                 390                 395                 400

Met His Val Ala Asp Met Leu Val Lys Val Asn Ala Leu Ile Lys Asp
                405                 410                 415

Arg Glu Gly Tyr Ala Pro Gly Thr Glu Phe His Arg Cys Lys Glu Met
```

-continued

```
                420                 425                 430
        Ser Glu Tyr Cys Ser Thr Leu Cys Arg His Leu Tyr Leu Phe Pro Gly
                435                 440                 445

His Pro Pro Thr
                450

<210> SEQ ID NO 11
<211> LENGTH: 303
<212> TYPE: PRT
<213> ORGANISM: Homo sapiens

<400> SEQUENCE: 11

Met Ala Asp Asp Gln Gly Cys Ile Glu Glu Gln Gly Val Glu Asp Ser
1               5                   10                  15

Ala Asn Glu Asp Ser Val Asp Ala Lys Pro Asp Arg Ser Ser Phe Val
            20                  25                  30

Pro Ser Leu Phe Ser Lys Lys Lys Asn Val Thr Met Arg Ser Ile
        35                  40                  45

Lys Thr Thr Arg Asp Arg Val Pro Thr Tyr Gln Tyr Asn Met Asn Phe
    50                  55                  60

Glu Lys Leu Gly Lys Cys Ile Ile Ile Asn Asn Lys Asn Phe Asp Lys
65                  70                  75                  80

Val Thr Gly Met Gly Val Arg Asn Gly Thr Asp Lys Asp Ala Glu Ala
                85                  90                  95

Leu Phe Lys Cys Phe Arg Ser Leu Gly Phe Asp Val Ile Val Tyr Asn
            100                 105                 110

Asp Cys Ser Cys Ala Lys Met Gln Asp Leu Leu Lys Lys Ala Ser Glu
        115                 120                 125

Glu Asp His Thr Asn Ala Ala Cys Phe Ala Cys Ile Leu Leu Ser His
    130                 135                 140

Gly Glu Glu Asn Val Ile Tyr Gly Lys Asp Gly Val Thr Pro Ile Lys
145                 150                 155                 160

Asp Leu Thr Ala His Phe Arg Gly Asp Arg Cys Lys Thr Leu Leu Glu
                165                 170                 175

Lys Pro Lys Leu Phe Phe Ile Gln Ala Cys Arg Gly Thr Glu Leu Asp
            180                 185                 190

Asp Gly Ile Gln Ala Asp Ser Gly Pro Ile Asn Asp Thr Asp Ala Asn
        195                 200                 205

Pro Arg Tyr Lys Ile Pro Val Glu Ala Asp Phe Leu Phe Ala Tyr Ser
    210                 215                 220

Thr Val Pro Gly Tyr Tyr Ser Trp Arg Ser Pro Gly Arg Gly Ser Trp
225                 230                 235                 240

Phe Val Gln Ala Leu Cys Ser Ile Leu Glu Glu His Gly Lys Asp Leu
                245                 250                 255

Glu Ile Met Gln Ile Leu Thr Arg Val Asn Asp Arg Val Ala Arg His
            260                 265                 270

Phe Glu Ser Gln Ser Asp Asp Pro His Phe His Glu Lys Lys Gln Ile
        275                 280                 285

Pro Cys Val Val Ser Met Leu Thr Lys Glu Leu Tyr Phe Ser Gln
    290                 295                 300

<210> SEQ ID NO 12
<211> LENGTH: 293
<212> TYPE: PRT
<213> ORGANISM: Homo sapiens
```

<400> SEQUENCE: 12

```
Met Ser Ser Ala Ser Gly Leu Arg Arg Gly His Pro Ala Gly Glu
1               5                   10                  15

Glu Asn Met Thr Glu Thr Asp Ala Phe Tyr Lys Arg Glu Met Phe Asp
            20                  25                  30

Pro Ala Glu Lys Tyr Lys Met Asp His Arg Arg Arg Gly Ile Ala Leu
        35                  40                  45

Ile Phe Asn His Glu Arg Phe Phe Trp His Leu Thr Leu Pro Glu Arg
    50                  55                  60

Arg Gly Thr Cys Ala Asp Arg Asp Asn Leu Thr Arg Arg Phe Ser Asp
65                  70                  75                  80

Leu Gly Phe Glu Val Lys Cys Phe Asn Asp Leu Lys Ala Glu Glu Leu
                85                  90                  95

Leu Leu Lys Ile His Glu Val Ser Thr Val Ser His Ala Asp Ala Asp
            100                 105                 110

Cys Phe Val Cys Val Phe Leu Ser His Gly Glu Gly Asn His Ile Tyr
        115                 120                 125

Ala Tyr Asp Ala Lys Ile Glu Ile Gln Thr Leu Thr Gly Leu Phe Lys
    130                 135                 140

Gly Asp Lys Cys His Ser Leu Val Gly Lys Pro Lys Ile Phe Ile Ile
145                 150                 155                 160

Gln Ala Cys Arg Gly Asn Gln His Asp Val Pro Val Ile Pro Leu Asp
                165                 170                 175

Val Val Asp Asn Gln Thr Glu Lys Leu Asp Thr Asn Ile Thr Glu Val
            180                 185                 190

Asp Ala Ala Ser Val Tyr Thr Leu Pro Ala Gly Ala Asp Phe Leu Met
        195                 200                 205

Cys Tyr Ser Val Ala Glu Gly Tyr Tyr Ser His Arg Glu Thr Val Asn
    210                 215                 220

Gly Ser Trp Tyr Ile Gln Asp Leu Cys Glu Met Leu Gly Lys Tyr Gly
225                 230                 235                 240

Ser Ser Leu Glu Phe Thr Glu Leu Leu Thr Leu Val Asn Arg Lys Val
                245                 250                 255

Ser Gln Arg Arg Val Asp Phe Cys Lys Asp Pro Ser Ala Ile Gly Lys
            260                 265                 270

Lys Gln Val Pro Cys Phe Ala Ser Met Leu Thr Lys Lys Leu His Phe
        275                 280                 285

Phe Pro Lys Ser Asn
    290
```

<210> SEQ ID NO 13
<211> LENGTH: 36
<212> TYPE: DNA
<213> ORGANISM: artificial
<220> FEATURE:
<223> OTHER INFORMATION: 1369_Casp3.1_BsmBI_fp

<400> SEQUENCE: 13
aacgtctctg atgaacagct acaagatgga ctaccc                              36

<210> SEQ ID NO 14
<211> LENGTH: 37
<212> TYPE: DNA
<213> ORGANISM: artificial
<220> FEATURE:
<223> OTHER INFORMATION: 1369_Casp3.1_2Stop_AscI_rp

```
<400> SEQUENCE: 14
aaggcgcgcc tattattttt cgaactgcgg gtggctc                              37

<210> SEQ ID NO 15
<211> LENGTH: 60
<212> TYPE: DNA
<213> ORGANISM: artificial
<220> FEATURE:
<223> OTHER INFORMATION: 1369_Casp3.1_pHILD2_fp

<400> SEQUENCE: 15
aacaattgtc tgccatcatg catcatcatc atcatcataa cagctacaag atggactacc    60

<210> SEQ ID NO 16
<211> LENGTH: 38
<212> TYPE: DNA
<213> ORGANISM: artificial
<220> FEATURE:
<223> OTHER INFORMATION: 1369_Casp3.1_pHILD2_rp

<400> SEQUENCE: 16
aacaattgtt attagagacc gtggtagaag tacagctc                            38
```